(12) United States Patent
Yonehara et al.

(10) Patent No.: US 8,026,078 B2
(45) Date of Patent: Sep. 27, 2011

(54) METHOD OF QUANTIFYING GLYCOSYLATED PROTEIN USING REDOX REACTION AND QUANTIFICATION KIT

(75) Inventors: Satoshi Yonehara, Kyoto (JP); Kaori Ishimaru, Kyoto (JP); Tsuguki Komori, Kyoto (JP)

(73) Assignee: ARKRAY Inc., Kyoto (JP)

( * ) Notice: Subject to any disclaimer, the term of this patent is extended or adjusted under 35 U.S.C. 154(b) by 397 days.

(21) Appl. No.: 10/501,291

(22) PCT Filed: Jan. 29, 2003

(86) PCT No.: PCT/JP03/00820
§ 371 (c)(1),
(2), (4) Date: Jul. 12, 2004

(87) PCT Pub. No.: WO03/064683
PCT Pub. Date: Aug. 7, 2003

(65) Prior Publication Data
US 2005/0042709 A1 Feb. 24, 2005

(30) Foreign Application Priority Data

Jan. 31, 2002 (JP) ................................. 2002-023897
Jan. 31, 2002 (JP) ................................. 2002-023898

(51) Int. Cl.
*C12Q 1/26* (2006.01)
(52) U.S. Cl. ............. 435/25; 435/23; 435/191; 436/67; 436/86
(58) Field of Classification Search .................. None
See application file for complete search history.

(56) References Cited

U.S. PATENT DOCUMENTS

| 5,556,788 | A | * | 9/1996 | Kwan et al. ............... 436/87 |
| 5,712,138 | A | | 1/1998 | Kato et al. |
| 5,731,206 | A | * | 3/1998 | Ledis et al. ............... 436/17 |
| 5,789,221 | A | | 8/1998 | Kato et al. |
| 5,824,527 | A | | 10/1998 | Kato et al. |
| 5,985,591 | A | | 11/1999 | Yonehara et al. |
| 6,033,867 | A | | 3/2000 | Kato et al. |
| 6,127,138 | A | * | 10/2000 | Ishimaru et al. ............... 435/23 |
| 6,790,665 | B2 | * | 9/2004 | Yonehara et al. ............... 436/66 |
| 2004/0248226 | A1 | | 12/2004 | Yonehara et al. |
| 2005/0101771 | A1 | | 5/2005 | Kouzuma et al. |

FOREIGN PATENT DOCUMENTS

| EP | 0166505 | | 1/1986 |
| EP | 1 002874 A2 | * | 5/2000 |
| JP | 60-214900 | | 10/1985 |
| JP | 7-289253 | | 11/1995 |
| JP | 8-154672 | | 6/1996 |
| JP | 8-336386 | | 12/1996 |
| JP | 97/20039 | | 6/1997 |
| JP | 10-313893 | | 12/1998 |
| JP | 2000-333696 | | 12/2000 |
| JP | 2001-054398 | | 2/2001 |
| JP | 2001-204495 | | 7/2001 |

OTHER PUBLICATIONS

Montellano et al. (1988) Biochemistry, vol. 27, pp. 5470-5476.*
Yoshida et al., Eur. J. Biochem., 1996, vol. 242, 499-505.*
Fry et al.. J. Nutr., 1982, vol. 112, p. 1631-p. 1737.*
Fujiwara et al., "Conversion of Substrate Specificity of Glycated Amino Acid Oxidase Derived from *Fusarium oxysporum*", Annual Meeting 2000, The Society for Biotechnology, Japan with English translation.
Notification of Reason for Rejection issued in corresponding Japanese Application No. 2003-564273 and mailed Mar. 26, 2009, with an English Translation—8 pages.

* cited by examiner

*Primary Examiner* — Kade Ariani
(74) *Attorney, Agent, or Firm* — Morgan, Lewis & Bockius LLP

(57) ABSTRACT

The present invention provides a method of measuring a glycated protein in a sample using a redox reaction, by which the glycated protein can be measured accurately with high sensitivity. In order to remove a glycated amino acid present in the sample other than the glycated protein, the glycated amino acid is degraded in advance by causing a fructosyl amino acid oxidase to act thereon, and thereafter, a fructosyl amino acid oxidase is caused to act on the glycated protein in the presence of a tetrazolium compound and sodium azide to cause a redox reaction. The amount of the glycated protein is determined by measuring the redox reaction. As the glycated protein, glycated hemoglobin is preferable.

27 Claims, 1 Drawing Sheet

METHOD OF QUANTIFYING GLYCOSYLATED PROTEIN USING REDOX REACTION AND QUANTIFICATION KIT

TECHNICAL FIELD

The present invention relates to a method of measuring a glycated protein using a redox reaction and to a measuring kit.

BACKGROUND ART

Among various glycated proteins, glycated hemoglobin (glycated Hb) in blood serves as an important indicator in the diagnosis, treatment, etc. of diabetes, because it reflects the patient's past history of blood glucose levels.

Measurement of such glycated Hb has been carried out, for example, by high performance liquid chromatography (HPLC), a minicolumn method, an immunoassay, a dye method, or the like. According to these methods, the ratio of glycated Hb to total Hb or the amount of glycated Hb can be determined. However, the above-described HPLC has a problem in that, for example, it requires a dedicated apparatus for measuring glycated Hb, and the immunoassay and the dye method have problems in that, for example, cells used for measurement might be contaminated and the measurement sensitivity might not be sufficient.

On this account, measurement of a glycated protein such as glycated Hb using a redox reaction caused by an enzyme has been utilized in applications such as biochemical analyses and clinical tests, because it can be carried out easily without using a special measuring apparatus.

Such measurement of glycated Hb using a redox reaction is carried out, for example, in the following manner. First, a sample containing glycated Hb is treated with a fructosyl amino acid oxidase (hereinafter referred to as "FAOD") so that the FAOD acts on a glycation site of the glycated Hb, thereby causing hydrogen peroxide to be formed. The amount of the hydrogen peroxide corresponds to the amount of the glycated Hb. Subsequently, to the sample treated with the FAOD, a peroxidase (hereinafter referred to as "POD") and a reducing agent are added so that a redox reaction occurs between the hydrogen peroxide and the reducing agent with the POD as a catalyst. At this time, when a reducing agent that develops color when it is oxidized is used, the amount of the hydrogen peroxide can be determined by measuring the color developed. As a result, the amount of the glycated Hb in the sample can be determined.

DISCLOSURE OF INVENTION

However, such conventional methods do not exhibit sufficient measurement sensitivity. Furthermore, with regard to measurement accuracy, there have been problems in that more hydrogen peroxide may be formed than corresponds to glycated Hb actually contained in a sample and that, depending on the patient, the measured value of glycated Hb may leap up temporarily. Therefore, further improvement in the measurement accuracy is desired.

Therefore, it is an object of the present invention to provide a method of measuring a glycated protein in a sample using a redox reaction, by which the glycated protein can be measured accurately with high sensitivity. Furthermore, it is another object of the present invention to provide a measuring kit to be used in the method, capable of achieving excellent measurement accuracy and measurement sensitivity and having excellent operability.

In order to achieve the above object, the present invention provides a method of measuring an amount of a glycated protein in a sample, including: causing a FAOD to act on a glycated amino acid present in the sample other than the glycated protein so as to remove the glycated amino acid by degrading it; then causing a FAOD to act on the glycated protein to cause a redox reaction in the presence of a tetrazolium compound and sodium azide; and measuring the redox reaction to determine the amount of the glycated protein.

It is to be noted that "FAOD" merely is a generic name and the substrate thereof is not limited to glycated amino acids. For example, FAODs act also on glycated proteins and glycated peptides. Hereinafter, a FAOD used for degrading the glycated amino acid is referred to as a "degradation FAOD" and a FAOD caused to act on the glycated protein to measure it is referred to as a "measurement FAOD" in the present invention.

The inventors of the present invention have conducted in-depth research to improve the accuracy of the measurement and finally found out the following fact. In whole blood, not only a glycated protein but also a free-state glycated amino acid is present inherently. FAODs also act on such a glycated amino acid. Thus, when a glycated protein is measured using a FAOD as described above, a redox reaction occurs not only between the glycated protein and the FAOD but also between the glycated amino acid and the FAOD, so that the measured value of the glycated protein apparently increases. Moreover, regarding the above-described problem that some patients show considerable variation in the measured value depending on the time when the blood is collected even though the measurement is carried out by the above-described method with respect to the whole blood samples collected from the same patient under the same conditions, the inventors of the present invention also found out the following fact. Such a problem is seen mainly in patients after being put on an intravenous drip or the like. For example, if a saccharide such as glucose and any of various amino acids are administered via an intravenous drip or the like, a glycated amino acid is formed from such exogenous substances. As a result, the glycated amino acid increases temporarily, which causes the above-described variation in measured value. Thus, based on these findings, the inventors of the present invention discovered that, even if a whole blood sample contains a glycated amino acid present homeostatically or an exogenous glycated amino acid present temporarily, the increase in the measured value due to the glycated amino acid as described above can be suppressed by causing a degradation FAOD to act on the glycated amino acid to degrade it as in the present invention. This allows the accuracy of measurement to be improved. In addition, since this allows blood to be collected any time regardless of whether or not the patients were put on an intravenous drip, the burden on patients can be reduced. Moreover, by carrying out the redox reaction in the presence of the tetrazolium compound and the sodium azide, the measurement sensitivity is improved, although the mechanism is unknown. Therefore, according to the method that is excellent in measurement accuracy and measurement sensitivity as described above, the reliability of various glycated proteins as indicators is improved. Thus, the method is useful in the field of clinical medicine and the like.

In the present invention, the glycated protein preferably is glycated Hb. This is because the above-described method of the present invention can improve the reliability of glycated Hb as an indicator in the diagnosis of diabetes and thus can serve as a useful method in the field of clinical medicine and the like.

Examples of the method for measurement according to the present invention include a first method in which FAODs having substrate specificities different from each other are caused to act on the glycated amino acid and the glycated protein, respectively, and a second method in which FAODs having the same substrate specificity are caused to act on them.

As described later, there are various FAODs, e.g., a FAOD that acts on a glycated α-amino group, a FAOD that acts on a glycated amino group in a side chain (hereinafter also referred to as a "glycated side-chain amino group) of an amino acid residue such as a lysine residue or an arginine residue, and a FAOD that acts on both a glycated α-amino group and a glycated side-chain amino group, and their substrate specificities vary depending on the type of FAODs. When the glycated protein is glycated Hb, for example, the amount of the glycated Hb can be measured by causing a FAOD to act on any of the glycated α-amino group, the glycated side-chain amino group, and both the glycated α-amino group and the glycated side-chain amino group.

In the first method of the present invention, it is preferable that the degradation FAOD caused to act on the glycated amino acid has a substrate specificity different from that of the measurement FAOD caused to act on the glycated protein. With this configuration, the glycated amino acid is degraded with the degradation FAOD, and then, with regard to the glycated protein, the glycation site thereof not subjected to the action of the degradation FAOD is subjected to the action of the measurement FAOD having a substrate specificity different from that of the degradation FAOD. Thus, the influence of the glycated amino acid can be eliminated so that the accuracy of the measurement is improved.

Specifically, it is preferable that the degradation FAOD is specific for a glycated α-amino group, and the measurement FAOD is specific for a glycated α-amino group and a glycated side chain of an amino acid residue, for example. Since the measurement FAOD acts on both a glycated α-amino group and a glycated side-chain amino group, it also acts on the glycated amino acid having a glycated α-amino group when used in conventional methods, as described above. However, in the present invention, since the glycated amino acid is degraded with the degradation FAOD specific for a glycated α-amino group in advance, there is no chance that the measurement FAOD may act thereon. As a result, the seeming increase in the measured value is suppressed so that the accuracy of the measurement is improved. Moreover, although the measurement FAOD acts on both a glycated α-amino group and a glycated side-chain amino group as described above, since the glycated α-amino group of the glycated protein also is degraded with the degradation FAOD, it is possible to cause the measurement FAOD to act only on the glycated side-chain amino group of the glycated protein. Therefore, this method particularly is useful for measurement of glycated Hb that is characterized by the amount of the glycated side-chain amino group.

When using different FAODs as described above, it is preferable that the glycated protein is degraded with a protease to give a degradation product of the glycated protein either before or after causing the FAOD to act on the glycated amino acid and the measurement FAOD caused to act on the glycated protein is caused to act on this degradation product so as to cause the above-described redox reaction. The degradation of the glycated protein with a protease is carried out because FAODs have properties that they act on glycated amino acids and shorter glycated peptide fragments more easily than on glycated proteins. Moreover, the reason why the protease treatment may be carried out either before or after the degradation treatment of the glycated amino acid is that, since the measurement FAOD also can act on the glycation site other than that on which the degradation FAOD acts as described above, the degradation FAOD treatment does not have any influence on the measurement of the glycated protein itself.

Next, as the second method of the present invention, it is preferable that the glycated protein is degraded with a protease to give a degradation product of the glycated protein after causing the degradation FAOD to act on the glycated amino acid, and the above-described redox reaction is caused by adding the FAOD having the same substrate specificity as the degradation FAOD so that it acts on the degradation product. That is, in the second method for measurement, the degradation FAOD and the measurement FAOD are the same.

Specifically, it is preferable that the degradation FAOD is inactivated with the protease. As described above, FAODs have properties that they act on glycated amino acids and shorter glycated peptide fragments more easily than on a glycated protein as an analyte. Thus, it can be said based on chemical kinetics of enzymes that, even if a degradation FAOD is added, it hardly acts on the glycated protein within a treatment period for degrading the glycated amino acid. However, if the activity of the degradation FAOD still remains during the protease treatment of the glycated protein performed subsequently, the remaining degradation FAOD may act on a glycated protein degradation product (i.e., a glycated amino acid and a glycated peptide fragment of the glycated protein) obtained while the glycated protein is being degraded with the protease. Therefore, when the measurement FAOD is added after the protease treatment, part of the glycated protein degradation product already is subjected to the action of the remaining degradation FAOD. As a result, contrary to what is intended, the accuracy of the measurement may be deteriorated. However, if the protease treatment performed to degrade the glycated protein serves to inactivate the remaining degradation FAOD at the same time as described above, the glycated protein degradation product obtained by the protease treatment remains unreacted with the degradation FAOD and thus can react with the measurement FAOD added subsequently. As a result, the accuracy of the measurement can be improved.

On the other hand, as a third method for measurement, highly accurate measurement also can be realized by, for example, adjusting the amounts of the degradation FAOD and the measurement FAOD to be added to the sample without inactivating the degradation FAOD by the protease treatment as described above. In this case, the ratio (activity ratio A:B) of the degradation FAOD (A) to the measurement FAOD (B) preferably is set in the range from 1:10 to 1:1000. When the ratio is in the above-described range, if the degradation FAOD remains during the protease treatment, the remaining degradation FAOD hardly acts on a glycated protein degradation product, as understood from the chemical kinetics of enzymes.

In the method for measurement according to the present invention, as the protease, at least one protease selected from metalloproteinases, bromelain, papain, trypsin, proteinase K, subtilisin, aminopeptidase, and protease derived from *Bacillus subtilis* can be used.

When the glycated protein is glycated Hb, the protease preferably is at least one protease that degrades the glycated Hb selectively and is selected from the group consisting of metalloproteinases, bromelain, papain, trypsin derived from porcine pancreas, and protease derived from *Bacillus subtilis*. Among these, metalloproteinases and protease derived from *Bacillus subtilis* are preferable, and metalloproteinases are more preferable. When the analyte is glycated Hb, the glycated Hb alone can be measured by using such a protease, because glycated proteins and glycated peptides other than the glycated Hb hardly are degraded with the protease and thus a FAOD hardly acts on the glycated proteins and the like other than the glycated Hb.

In the method of the present invention, it is preferable that the tetrazolium compound (C) and the sodium azide (D) are present at a ratio (molar ratio C:D) in the range from 20:3 to 20:12. Furthermore, it is preferable that a final concentration of the tetrazolium compound in a reaction solution of the redox reaction is in the range from 0.5 to 2.5 mmol/l, and a final concentration of the sodium azide in the reaction solution is in the range from 0.13 to 1.3 mmol/l.

In the method for measurement according to the present invention, it is preferable that a solution containing the tetrazolium compound and the sodium azide is aged and then is added to the sample because this allows still further improvement in the sensitivity. In this case, it is preferable that the solution is aged at a temperature in the range from 20° C. to 60° C. Furthermore, it is preferable that the solution is aged for 6 to 120 hours.

In the present invention, the measurement of the redox reaction is not particularly limited, and may be, for example, measurement of an amount of hydrogen peroxide formed by causing the FAOD to act on the glycated protein. The amount of the hydrogen peroxide is determined by causing a redox reaction between the hydrogen peroxide and a substrate that develops color by oxidation (color-developing substrate) and then measuring the amount of the color developed by the color-developing substrate. As the color-developing substrate, N-(carboxymethylaminocarbonyl)-4,4'-bis (dimethylamino)diphenylamine sodium salt (hereinafter also referred to as "DA-64") can be used, for example.

When DA-64 is used, it is preferable that the DA-64 is added to the reaction solution in the presence of a surfactant. Also, it is preferable that the concentration of the tetrazolium compound in the reaction solution is in the range from 0.5 to 8 mmol/l, the concentration of the sodium azide is in the range from 0.08 to 0.8 mmol/l, the concentration of the surfactant is in the range from 0.3 to 10 mmol/l, and a pH of the reaction solution is in the range from 7.0 to 8.5.

It is one of the features of the present invention that the redox reaction is caused in the presence of a tetrazolium compound and sodium azide in order to improve the measurement sensitivity. However, when DA-64 is used as the color-developing substrate, a color development error of the DA-64 may occur due to the presence of the tetrazolium compound and sodium azide with the DA-64. Such color development error leads to an increase in background in the measurement of the color developed and to a shortage of the DA-64 even though the amount of the DA-64 added is sufficient. However, when the DA-64 is added in the presence of the surfactant and the concentrations of the respective components and the pH of the reaction solution are set in the above-described ranges, the increase in background can be suppressed so that the measurement can be carried out still more accurately.

In the method for measurement according to present invention, the type of the sample is not particularly limited. The method also can be applied to samples other than whole blood, plasma, serum, and blood cells, e.g. biological samples such as urine and spinal fluid, drinks such as juices, and foods such as soy sauce and Worcestershire sauce. Among these, the method particularly is useful for a whole blood sample and a blood cell sample. For example, when glycated Hb in erythrocytes is to be measured, whole blood itself may be hemolyzed to prepare a sample, or erythrocytes may be separated from whole blood and hemolyzed to prepare a sample.

Examples of the glycated protein as the analyte include glycated Hb as described above and glycated albumin. Among these, glycated Hb is preferable.

Next, the present invention provides a method of determining a ratio of glycated Hb to Hb. The method includes: measuring an amount of glycated Hb in a sample by the above-described method of measuring glycated Hb according to the present invention; measuring an amount of Hb in the sample; and then calculating the ratio of the glycated Hb to the Hb using the amount of the glycated Hb and the amount of the Hb thus measured. According to the present invention, the amount of the glycated Hb can be measured with high accuracy and hence, a highly reliable value of the ratio of the glycated Hb can be obtained. It is to be noted here that the "amount of Hb" refers to the total amount including both the amount of glycated Hb and the amount of non-glycated Hb.

In the present invention, the method of measuring the amount of Hb is not particularly limited, but preferably is a method including: denaturing Hb in a sample with a tetrazolium compound to give denatured Hb; measuring an absorbance of the sample at an absorption wavelength specific to the denatured Hb; and calculating an amount of the Hb in the sample from this absorbance. The Hb that is not yet denatured (hereinafter, referred to as "undenatured Hb") exhibits various absorption wavelengths depending on its state, e.g., the state where it is bound to oxygen, the state where it is not bound to oxygen, etc. Therefore, it is difficult to determine the amount of Hb accurately by merely measuring the absorbance. In contrast, the denatured Hb obtained by the treatment with the tetrazolium compound is stable and exhibits the absorption maximum at a wavelength falling within a certain range. Thus, according to the method of the present invention, the amount of Hb can be measured easily and accurately. Therefore, by using the above-described highly reliable values of the amount of the glycated Hb and the amount of the Hb, a still more reliable value of the ratio of the glycated Hb to the Hb can be obtained.

The method of measuring a glycated protein according to the present invention also can be used to measure HbAlc. The amount of HbAlc in a sample can be determined in the following manner, for example. First, a calibration curve is prepared based on a correlation between an amount of glycated Hb obtained by the method of measuring a glycated protein according to the present invention and an amount of HbAlc. The amount of glycated Hb in a sample is measured by the method of the present invention and the obtained measured value is substituted into the calibration curve to determine an amount of HbAlc in the sample.

The inventors of the present invention have conducted in-depth researches and finally found that there is a strong correlation between an amount of glycated Hb in whole blood obtained by the method of measuring an amount of glycated Hb according to the present invention and an amount of HbAlc in the same sample. HbAlc is glycated Hb in which the N-terminal α-amino group in the β-chain of Hb is glycated. In glycated Hb, HbAlc serves as a particularly important indicator in the diagnosis etc. of diabetes. According to conventional methods of measuring HbAlc, it is necessary to cause a FAOD to act specifically on the glycated N-terminal α-amino group in the β-chain as a glycation site characteristic to HbAlc and then to measure the redox reaction caused by the FAOD. To this end, special techniques are required because it is necessary that the FAOD used has a high substrate specificity to the glycated α-amino group and that the FAOD acts on the glycated α-amino group sufficiently, for example. In contrast, according to the present invention, the amount of HbAlc can be determined based on the amount of glycated Hb measured with high accuracy. This enables accurate and easy measurement of HbAlc. As a result, the measurement of HbAlc can be made practical in clinical tests etc.

Next, the present invention provides a measuring kit used for measuring a glycated protein using a redox reaction, including: a pretreatment reagent for pretreating a sample, containing a FAOD; and a color-developing reagent containing a FAOD, an oxidoreductase, and a color-developing substrate.

As described above, the inventors of the present invention found out the cause of the problem regarding the measurement accuracy. Then, the inventors of the present invention discovered that, even though a whole blood sample contains a glycated amino acid present homeostatically or an exogenous glycated amino acid present temporarily, if a FAOD is contained in the pretreatment reagent as in the present invention, the glycated amino acid in the sample is degraded by adding the pretreatment reagent to the sample prior to the redox reaction and thus the increase in the measured value due to the glycated amino acid as described above can be suppressed. Therefore, by using a measuring kit according to the present invention, the measurement of a glycated protein using a redox reaction can be carried out quickly and simply and besides, with high accuracy. Moreover, with respect to a blood sample obtained from a patient after being put on an intravenous drip, the measurement can be carried out under the same conditions. Furthermore, since the measuring kit according to the present invention can carry out measurement with high accuracy as described above, it can increase the reliability of various glycated proteins as indicators and thus can serve as a useful measuring kit in the field of clinical medicine and the like.

In the measuring kit according to the present invention, it is preferable that an analyte is glycated Hb. This is because the reliability of glycated Hb as an indicator in the diagnosis of diabetes is increased by this measuring kit so that glycated Hb becomes more useful in the field of clinical medicine and the like.

In the present invention, a FAOD contained in the pretreatment reagent degrades the glycated amino acid. Thus, such a FAOD hereinafter also is referred to as a "degradation FAOD" as described above. On the other hand, a FAOD contained in the color-developing reagent is caused to act on a glycated protein, and thus hereinafter also is referred to as a "measurement FAOD".

It is preferable that the measuring kit according to the present invention further includes a protease reagent containing a protease. FAODs have properties that they act on glycated amino acids and shorter glycated peptide fragments more easily than on glycated proteins. Therefore, by degrading a glycated protein in a sample by this protease reagent, the measurement FAOD can act on the glycated protein still more easily, which allows the measurement accuracy to be further improved. As the protease, the same proteases as used in the method of measuring a glycated protein according to the present invention can be used.

In the measuring kit according to the present invention, it is preferable that the protease reagent further contains a tetrazolium compound and sodium azide. When the protease reagent contains a tetrazolium compound and sodium azide, the measurement sensitivity can be improved. Besides, the influence of reducing substances and the like contained in the sample on a redox reaction can be eliminated by the tetrazolium compound, thereby allowing the measurement accuracy to be improved.

When the protease contained in the protease reagent is a metalloproteinase, it is preferable that the protease reagent further contains Ca and Na. Preferably, the concentration of the metalloproteinase is in the range from 100 to 40,000 KU/l, the concentration of Ca is in the range from 0.1 to 50 mmol/l, and the concentration of Na is in the range from 5 to 1000 mmol/l. When the metalloproteinase, Ca, and Na are present in the protease reagent so that their concentrations fall in the above-described ranges, the stability of the metalloproteinase is improved. As a result, not only at low temperatures but also at ordinary temperatures, the metalloproteinase is prevented from being inactivated and thus can be stored stably, for example. The ionization of Ca and Na to $Ca^{2+}$ and $Na^+$, respectively, may occur during the use of the protease reagent.

The concentrations of the respective components in the protease reagent are not limited to the above-described ranges. For example, it is preferable that the ratio between the respective components is the same as that between the respective concentration ranges. This is because the added amount of the respective components necessary for the reaction can be adjusted by adjusting the proportion of the protease reagent to the reaction solution (i.e., dilution ratio). The same applies to other components and other reagents.

Examples of the measuring kit according to the present invention include a first measuring kit in which a degradation FAOD contained in the pretreatment reagent and a measurement FAOD contained in the color-developing reagent have substrate specificities different from each other, and second and third measuring kits in which the degradation FAOD and the measurement FAOD have the same substrate specificity.

In the first measuring kit according to the present invention, it is preferable that the degradation FAOD contained in the pretreatment reagent has a substrate specificity different from that of the measurement FAOD contained in the color-developing reagent. When the measuring kit having such a configuration is used, the glycated amino acid is degraded with the degradation FAOD, and then, with regard to the glycated protein, the glycation site thereof not subjected to the action of the degradation FAOD is subjected to the action of the measurement FAOD. Thus, the influence of the glycated amino acid can be eliminated so that the accuracy of the measurement is improved.

Specifically, it is preferable that the degradation FAOD is specific for a glycated α-amino group, and the measurement FAOD is specific for a glycated α-amino group and a glycated side-chain amino group, for example. Since the measurement FAOD acts on both a glycated α-amino group and a glycated side-chain amino group, it also acts on the glycated amino acid having a glycated α-amino group when used in conventional methods, as described above. However, when the measuring kit according to the present invention is used, since the glycated amino acid is degraded with the degradation FAOD specific for a glycated α-amino group in advance by the treatment with the pretreatment reagent, there is no chance that the measurement FAOD may act thereon. As a result, the seeming increase in the measured value is suppressed so that the accuracy of the measurement is improved. Moreover, although the measurement FAOD acts on both a glycated α-amino group and a glycated side-chain amino group as described above, the glycated α-amino group of the glycated protein also is degraded with the degradation FAOD in advance. Thus, when the sample is treated with the color-developing reagent according to the present invention, the measurement FAOD can act only on the glycated side-chain amino group of the glycated protein. Therefore, this measuring kit particularly is useful for measurement of glycated Hb that is characterized by the amount of the glycated side-chain amino group. Such a measuring kit can be used in the first method of measuring a glycated protein according to the present invention.

In the second measuring kit according to the present invention, the degradation FAOD contained in the pretreatment reagent and the measurement FAOD contained in the color-developing reagent have the same substrate specificity. Preferably, the second measuring kit further includes a protease reagent containing a protease for degrading a glycated protein and inactivating the degradation FAOD by digesting it.

The second measuring kit can be used in the following manner, for example. First, the pretreatment reagent is added to a sample so that the degradation FAOD acts on a glycated amino acid. Thereafter, the protease reagent is added so that the protease contained therein degrades a glycated protein and, at the same time, degrades the remaining degradation FAOD by digesting it. Then, the color-developing reagent is added so that the measurement FAOD acts on the glycated protein degradation product obtained by the protease treatment to cause the above-described redox reaction.

As described above, FAODs have properties that they act on glycated amino acids and shorter glycated peptide fragments more easily than on a glycated protein as the analyte. Thus, it can be said based on chemical kinetics of enzymes that, even though the pretreatment reagent containing the degradation FAOD is added, the degradation FAOD hardly acts on the glycated protein within a treatment period for degrading the glycated amino acid. However, if the activity of the degradation FAOD still remains during the treatment with the protease reagent performed subsequently, the remaining degradation FAOD acts on a glycated protein degradation product (i.e., a glycated amino acid and a glycated peptide fragment of the glycated protein) obtained while the glycated protein is being degraded with the protease. Therefore, when the color-developing reagent containing the measurement FAOD is added after the treatment with the protease reagent, part of the glycated protein degradation product already is subjected to the action of the degradation FAOD. As a result, contrary to what is intended, the accuracy of the measurement may be deteriorated. However, if the protease reagent that serves to degrade the glycated protein and inactivate the degradation FAOD by digesting it is further included as in the second measuring kit according to the present invention, the glycated protein degradation product remains unreacted with the degradation FAOD and thus can react with the measurement FAOD in the color-developing reagent added subsequently. As a result, the accuracy of the measurement is improved. Such a measuring kit can be used in the second method of measuring a glycated protein according to the present invention.

In the third measuring kit according to the present invention, the degradation FAOD and the measurement FAOD also have the same substrate specificity. However, the third measuring kit can realize highly accurate measurement without inactivating the degradation FAOD with a protease reagent as in the second measuring kit by, for example, adjusting the concentration of the degradation FAOD in the pretreatment reagent and the concentration of the measurement FAOD in the color-developing reagent. In this case, the concentrations of the degradation FAOD in the pretreatment reagent and the measurement FAOD in the color-developing reagent preferably are set so that the ratio (activity ratio A:B) of the degradation FAOD (A) to the measurement FAOD (B) in, for example, a color-developing reaction solution obtained finally falls in the range from 1:10 to 1:1000. When the ratio is in the above-described range, even if the degradation FAOD remains during the treatment with the protease reagent, the remaining degradation FAOD hardly acts on a glycated protein, as understood from the chemical kinetics of enzymes. Such a measuring kit can be used in the third method of measuring a glycated protein according to the present invention. In the measuring kit according to the present invention, as the color-developing substrate, a substrate that develops color by oxidization, a substrate that develops color by reduction, or the like can be used, for example. Among these, a substrate that develops color by oxidization is preferable, and specifically, N-(carboxymethylaminocarbonyl)-4,4'-bis (dimethylamino) diphenylamine sodium salt is preferable.

In the case where the DA-64 is used as the color-developing substrate, when the protease reagent contains a tetrazolium compound and sodium azide as described above, these three components are mixed with each other in the reaction system, which may cause a color development error of the DA-64. Such a color development error leads to an increase in background in the measurement of the color developed and to a shortage of the DA-64 even though the amount of the DA-64 added is sufficient. However, as described above, if the respective components are contained in the respective reagents so that their concentrations fall within the above-describe ranges, the color development error of the DA-64 in the reaction system is suppressed. As a result, the increase in background can be suppressed so that the measurement can be carried out still more accurately.

In the measuring kit according to the present invention, each of the pretreatment reagent, the protease reagent, and the color-developing reagent further may contain a surfactant.

Furthermore, it is preferable that each of the reagents further contains at least one buffer selected from the group consisting of CHES, MOPS, MES, Tris, phosphate, TES, TAPS, HEPES, HEPPSO, borate, triethanolamine, BES, MOPSO, EPPS, POPSO, ADA, PIPES, ACES, and Bis-Tris. Each of the reagents contains an enzyme. Thus, by adding the buffer, it is possible to cause the enzyme to act at an optimal pH, for example.

Specifically, it is preferable that the pretreatment reagent further contains at least one buffer selected from the group consisting of CHES, MOPS, TAPS, EPPS, phosphate, HEPPSO, POPSO, and borate, and that a pH of the pretreatment reagent is in the range from 8.0 to 10.0.

Furthermore, it is preferable that the protease reagent further contains at least one buffer selected from the group consisting of Tris, MES, DIPSO, TES, POPSO, HEPES, MOPSO, Bis-Tris, MOPS, ADA, PIPES, ACES, and phosphate, and that a pH of the protease reagent is in the range from 5.0 to 7.0.

Still further, it is preferable that the color-developing reagent further contains at least one buffer selected from the group consisting of MES, Tris, phosphate, MOPS, TES, HEPES, HEPPSO, and EPPS, and that a pH of the color-developing reagent is in the range from 6.0 to 9.0.

Preferably, the color-developing reagent further contains sodium azide because it can prevent the color development error of the developing substrate such as DA-64, for example.

Preferably, the pretreatment reagent further contains at least one of uricase and bilirubin oxidase. When the pretreatment reagent contains uricase, uric acid contained in a sample can be degraded, and when the pretreatment reagent contains bilirubin oxidase, bilirubin in a sample can be degraded, for example. The uric acid and bilirubin have reducing power. Thus, by degrading the uric acid and bilirubin as described above, the influence of the reducing substances can further be eliminated, which allows the accuracy of measurement to further be improved.

Examples of the specific composition of each of the reagents in the measuring kit according to the present invention will be described below.

For example, in the pretreatment reagent, it is preferable that the FAOD is specific for a glycated α-amino group and that the concentration of the FAOD is in the range from 10 to 5000 U/l and the concentration of the buffer is in the range from 5 to 200 mmol/l. Furthermore, a pH of the pretreatment reagent preferably is in the range from 8.0 to 10.0.

For example, in the protease reagent, it is preferable that the concentration of the metalloproteinase is in the range from 100 to 10,000 KU/l, the concentration of the tetrazolium compound is in the range from 0.1 to 10 mmol/l, the concentration of the sodium azide is in the range from 0.08 to 4 mmol/l, the concentration of Ca is in the range from 0.1 to 50 mmol/l, the concentration of Na is in the range from 5 to 1000 mmol/l, and the concentration of the buffer is in the range from 0.1 to 500 mmol/l. Furthermore, a pH of the protease reagent preferably is in the range from 5.0 to 7.0.

For example, in the color-developing reagent, it is preferable that the FAOD is specific for a glycated α-amino group and a glycated side chain of an amino acid residue and that the concentration of the FAOD is in the range from 100 to 50,000 U/l, the concentration of a peroxidase is in the range from 0.1 to 400 KU/l, the concentration of N-(carboxymethylaminocarbonyl)-4,4'-bis(dimethylamino)diphenylamine sodium salt is in the range from 0.02 to 2 mmol/l, and the concentration of the buffer is in the range from 10 to 500 mol/l. Furthermore, a pH of the color-developing reagent preferably is in the range from 6 to 9.

The measuring kit according to the present invention is applicable to the same samples as in the method of measuring a glycated protein according to the present invention. Also, the measuring kit is applicable to the same analytes as in the method of measuring a glycated protein according to the present invention, and glycated Hb is preferable as an analyte.

Each of the reagents in the measuring kit according to the present invention may be a liquid reagent obtained by dissolving respective components in a aqueous solvent or a dry reagent to be dissolved in an aqueous solvent before use.

BEST MODE FOR CARRYING OUT THE INVENTION

Figure 1:
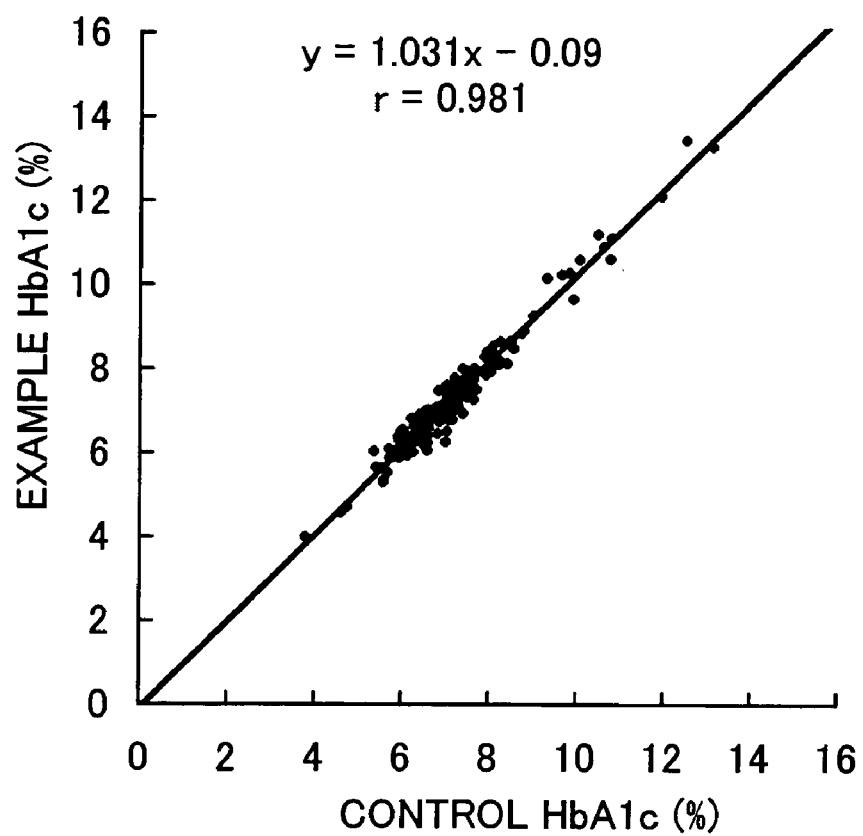
FIG. 1 is a graph showing the correlation between the amount of HbA1c measured by an enzymatic method according to one example of the present invention and that measured by HPLC.

In the method for measurement and the measuring kit according to the present invention, FAODs catalyzing a reaction represented by Formula (1) below preferably are used. Examples of such FAODs include a FAOD specific for a glycated amine having a glycated α-amino group (hereinafter referred to as a "FAOD-α"), a FAOD specific for a glycated amine having a glycated amino group in a side chain of an amino acid residue (hereinafter referred to as a "FAOD-S"), and a FAOD specific for both a glycated protein having a glycated α-amino group and a glycated protein having a glycated amino group in a side of an amino acid residue (hereinafter referred to as a "FAOD-αS"). The "glycated amine" refers to a glycated protein, glycated peptide, glycated amino acid, and the like.

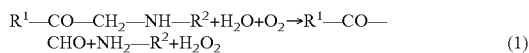  (1)

In Formula (1), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by

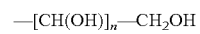

where n is an integer of 0 to 6.

In Formula (1), $R^2$ is not particularly limited. However, when the glycated amine is a glycated amino acid or a glycated peptide (including a glycated protein), there is a difference between the case where an α-amino group is glycated and the case where an amino group other than the α-amino group (i.e., an amino group in a side chain of an amino acid residue) is glycated.

In Formula (1), when an α-amino group is glycated, $R^2$ is an amino acid residue or a peptide residue represented by Formula (2) below. The above-described FAOD-α and FAOD-αS specifically catalyze the reaction represented by Formula (1) in this case.

  (2)

In Formula (2), $R^3$ denotes an amino-acid side chain group. $R^4$ denotes a hydroxyl group, an amino acid residue, or a peptide residue, and can be represented, for example, by Formula (3) below. In Formula (3), n is an integer of 0 or more, and $R^3$ denotes an amino-acid side chain group as in the above. When n is an integer of more than 1, the amino-acid side chain groups may be either the same or different.

  (3)

In Formula (1), when an amino group other than the α-amino group is glycated (i.e., an amino-acid side chain group is glycated), $R^2$ can be represented by Formula (4) below. The above-described FAOD-S and FAOD-αS specifically catalyze the reaction represented by Formula (1) in this case.

  (4)

In Formula (4), $R^5$ denotes a portion other than the glycated amino group in the amino-acid side chain group. For example, when the glycated amino acid is lysine, $R^5$ is as follows.

For another example, when the glycated amino acid is arginine, $R^5$ is as follows.

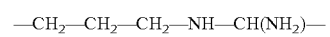

In Formula (4), $R^6$ denotes hydrogen, an amino acid residue, or a peptide residue, and can be represented, for example, by Formula (5) below. In Formula (5), n denotes an integer of 0 or more, and $R^3$ denotes an amino-acid side chain group as in the above. When n is an integer of more than 1, the amino-acid side chain groups may be either the same or different.

  (5)

In Formula (4), $R^7$ denotes a hydroxyl group, an amino acid residue, or a peptide residue, and can be represented, for example, by Formula (6) below. In Formula (6), n is an integer of 0 or more, and $R^3$ denotes an amino-acid side chain group as in the above. When n is an integer of more than 1, the amino-acid side chain groups may be either the same or different.

 (6)

Examples of the FAOD-α specific for a glycated α-amino group include a commercially available product named Fructosyl-Amino Acid Oxidase (FAOX-E) (manufactured by Kikkoman Corporation) and FAODs derived from the genus *Penicillium* (JP 8 (1996)-336386 A). Examples of the FAOD-S specific for a glycated side chain of an amino acid residue include FAODs derived from the genus *Fusarium* ("Conversion of Substrate Specificity of Amino Acid Oxidase Derived from *Fusarium oxysporum*" by Maki FUJIWARA et al., Annual Meeting 2000, The Society for Biotechnology, Japan). Furthermore, examples of FAOD-αS specific for both a glycated, α-amino group and a glycated side chain group of an amino acid residue include a commercially available product named FOD (manufactured by Asahi Chemical Industry Co., Ltd.), FAODs derived from the genus *Gibberella* (JP 8 (1996)-154672 A), FAODs derived from the genus *Fusarium* (JP 7 (1995)-289253 A), and FAODs derived from the genus *Aspergillus*.

The tetrazolium compound used in the present invention preferably contains ring substituents at least at two positions on its tetrazole ring, more preferably at three positions on its tetrazole ring, for example.

In the case where the tetrazolium compound contains ring substituents at least at two positions on its tetrazole ring as described above, it is preferable that the ring substituents are at the 2-position and 3-position on the tetrazole ring. Further, in the case where the tetrazolium compound contains ring substituents at three positions on its tetrazole ring, it is preferable that the ring substituents are at the 2-position, 3-position, and 5-position on the tetrazole ring.

Further, it is preferable that at least two ring substituents of the tetrazolium compound have a benzene ring structure. Besides the benzene ring structure, the ring substituents may have a resonance structure with S or O being contained in the ring skeleton, for example. Examples of the ring substituents with such a resonance structure include a thienyl group, thiazoyl group, and the like.

Furthermore, it is preferable that the tetrazolium compound contains ring substituents at least at three positions on its tetrazole ring and at least two of the ring substituents have a benzene ring structure.

Still further, it is preferable that at least one ring substituent contains a functional group, and a larger number of functional groups are more preferable.

As the functional group, an electron-withdrawing functional group preferably is used. For example, a halogen group, ether group, ester group, carboxy group, acyl group, nitroso group, nitro group, hydroxy group, sulfo group, and the like can be used. Other than these, characteristic groups containing oxygen such as a hydroperoxy group, oxy group, epoxy group, epidioxy group, oxo group, and the like; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, isothiocyanate group, and the like also can be used, for example. Among these electron-withdrawing functional groups, a nitro group, sulfo group, halogen group, carboxy group, hydroxy group, methoxy group, ethoxy group are preferable. Further, in addition to the above-described electron-withdrawing functional groups, unsaturated hydrocarbon groups such as a phenyl group ($C_6H_5$—), styryl group ($C_6H_5CH=CH$—), and the like also can be used, for example. It is to be noted that the functional groups may have been ionized by dissociation.

Still further, it is preferable that the tetrazolium compound contains benzene rings at the 2-position and 3-position on its tetrazole ring and at least one of the benzene rings contains at least one functional group selected from the group consisting of a halogen group, carboxy group, nitro group, hydroxy group, sulfo group, methoxy group, and ethoxy group. It is to be noted here that both the benzene rings may have such a functional group. Further, the functional group may be contained at any positions (ortho-, meta-, para-) on each of the benzene rings. Furthermore, the number of the functional groups is not particularly limited, and the benzene ring may have either the same or different functional groups.

Examples of the tetrazolium compound containing ring substituents having a benzene ring structure at the 2-position, 3-position, and 5-position on its tetrazole ring include:

2-(4-iodophenyl)-3-(4-nitrophenyl)-5-(2,4-disulfophenyl)-2H-tetrazolium salt (hereinafter also referred to as "WST-3");

2-(4-iodophenyl)-3-(2,4-dinitrophenyl)-5-(2,4-disulfophenyl)-2H-tetrazolium salt;

2-(2-methoxy-4-nitrophenyl)-3-(4-nitrophenyl)-5-(2,4-disulfophenyl)-2H-tetrazolium salt;

2-(4-iodophenyl)-3-(4-nitrophenyl)-5-phenyl-2H-tetrazolium salt;

3,3'-(1,1'-biphenyl-4,4'-diyl)-bis(2,5-diphenyl)-2H-tetrazolium salt;

3,3'-[3,3'-dimethoxy-(1,1'-biphenyl)-4,4'-diyl]-bis[2-(4-nitrophenyl)-5-phenyl-2H-tetrazolium salt];

2,3-diphenyl-5-(4-chlorophenyl) tetrazolium salt;

2,5-diphenyl-3-(p-diphenyl) tetrazolium salt;

2,3-diphenyl-5-(p-diphenyl) tetrazolium salt;

2,5-diphenyl-3-(4-styrylphenyl) tetrazolium salt;

2,5-diphenyl-3-(m-tolyl) tetrazolium salt; and 2,5-diphenyl-3-(p-tolyl) tetrazolium salt.

The tetrazolium compound is not limited to those described above. In addition to the above-described tetrazolium compounds, a tetrazolium compound containing ring substituents having a benzene ring structure at two positions and a ring substituent having a structure other than the benzene ring structure at one position on its tetrazole ring also may be used. Examples of such a tetrazolium compound include:

2,3-diphenyl-5-(2-thienyl) tetrazolium salt;

2-benzothiazoyl-3-(4-carboxy-2-methoxyphenyl)-5-[4-(2-sulfoethyl carbamoyl)phenyl]-2H-tetrazolium salt;

2,2'-dibenzothiazoyl-5,5'-bis[4-di(2-sulfoethyl)carbamoylphenyl]-3,3'-(3,3'-dimethoxy-4,4'-biphenylene)ditetrazolium salt; and 3-(4,5-dimethyl-2-thiazoyl)-2,5-diphenyl-2H-tetrazolium salt.

Further, a tetrazolium compound containing ring substituents having a benzene ring structure at two positions and a substituent not having a ring structure at one position on its tetrazole ring also can be used. Examples of such a tetrazolium compound include:

2,3-diphenyl-5-cyano tetrazolium salt;

2,3-diphenyl-5-carboxy tetrazolium salt;

2,3-diphenyl-5-methyltetrazolium salt; and 2,3-diphenyl-5-ethyl tetrazolium salt.

Among the above-described tetrazolium compounds, the tetrazolium compounds containing three ring substituents are preferable as described above. Among these, the tetrazolium compounds containing three ring substituents having a benzene ring structure and a large number of electron-withdrawing functional groups are more preferable, and WST-3 is particularly preferable. It is to be noted here that the above-described tetrazolium compounds may be a salt or may have been ionized, for example. Moreover, the tetrazolium compound may be used either alone or in combinations of two or more types.

Hereinafter, the method of measuring a glycated protein according to the present invention will be described in detail with reference to the following Embodiments A-1 to A-5, in which glycated Hb in blood cells is measured.

Embodiment A-1

The present embodiment is an example where a FAOD-α is used to degrade a glycated amino acid while a FAOD-αS is used to measure glycated Hb and a redox reaction is caused in the presence of a tetrazolium compound and sodium azide.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited, and can be, for example, a method using a surfactant, a method using ultrasonic waves, and a method utilizing a difference in osmotic pressure. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are Triton X-100, Tween-20, Brij 35, and the like. The conditions of the treatment with the surfactant usually are as follows: when the concentration of blood cells in the solution to be treated is in the range from 1 to 10 vol %, the surfactant is added so that its concentration in the solution falls in the range from 0.01 to 5 wt %, and stirred at room temperature for about several seconds (about 5 seconds) to 10 minutes.

Next, a tetrazolium compound and sodium azide are added to the hemolyzed sample.

When the concentration of blood cells in the solution to be treated is in the range from 0.2 to 2 vol %, the tetrazolium compound preferably is added so that its concentration in the solution falls in the range from 0.005 to 400 mmol/l, more preferably from 0.02 to 100 mmol/l, and particularly preferably from 0.1 to 50 mmol/l. Specifically, when the tetrazolium compound is WST-3, it preferably is added so that its concentration falls in the range from 0.004 to 16 mmol/l, more preferably from 0.02 to 10 mmol/l, and particularly preferably from 0.1 to 5 mmol/l. The tetrazolium compound may be used either alone or in combinations of two or more types. By adding the tetrazolium compound and sodium azide as described above, the sensitivity becomes about 1.2 to 3 times greater than in the case where they are not added.

Furthermore, the tetrazolium compound (C) and the sodium azide (D) are added so that they are present at a ratio (molar ratio C:D), for example, in the range from 20:3 to 20:12, preferably from 20:5 to 20:11, and more preferably from 20:6 to 20:10.

The tetrazolium compound and sodium azide may be added to the hemolyzed sample simply as they are. However, in terms of simplicity in operation etc., it is preferable to use a tetrazolium compound solution obtained by dissolving the tetrazolium compound in a solvent and a sodium azide solution obtained by dissolving the sodium azide in a solvent, or a liquid mixture containing both the tetrazolium compound and the sodium azide (i.e., a tetrazolium compound-sodium azide liquid mixture).

The concentration of the tetrazolium compound or the sodium azide in the above-described respective solutions can be determined as appropriate depending on the diluting factor of the solutions when they are added to the hemolyzed sample, etc., but the concentration of the tetrazolium compound is, for example, in the range from 0.1 to 10 mmol/l, preferably from 0.6 to 5 mmol/l, and more preferably from 0.7 to 2.7 mmol/l, and the concentration of the sodium azide is, for example, in the range from 0.1 to 4 mmol/l, preferably from 0.15 to 1.8 mmol/l, and more preferably from 0.2 to 1.5 mmol/l. When the liquid mixture is to be used, the liquid mixture contains the tetrazolium compound (C) and the sodium azide (D), for example, at a ratio (molar ratio C:D) in the range from 20:3 to 20:12, preferably from 20:5 to 20:11, and more preferably from 20:6 to 20:10.

As the solvent of the above-described solutions, MOPS, MES, MOPSO, DIPSO, TES, POPSO, HEPES, phosphate buffer solutions, and the like can be used, for example. Among these, MOPS and MES buffer solutions are preferable. The pH of the solvent is, for example, in the range from 5.0 to 7.0, preferably from 5.5 to 6.5. The concentration of the buffer solution is, for example, in the range from 0.1 to 10 mmol/l, preferably from 1 to 5 mmol/l, and more preferably from 1 to 3 mmol/l. The final concentration of the buffer solution after being added to the hemolyzed sample is, for example, in the range from 0.7 to 9 mmol/l, preferably from 0.8 to 4.5 mmol/l, and more preferably from 0.8 to 2.7 mmol/l.

Moreover, the tetrazolium compound-sodium azide liquid mixture prepared preferably is left for a certain period before being added to the hemolyzed sample so as to be aged, because this allows still further improvement in sensitivity. According to this aging treatment, the sensitivity becomes, for example, about 1.2 to 3 times greater than in the case where the aging treatment is not performed.

In the aging treatment, the treatment temperature preferably is in the range from 40° C. to 60° C., more preferably from 50° C. to 60°, and the treatment period is, for example, in the range from 6 to 72 hours, preferably from 15 to 20 hours.

After the tetrazolium compound and sodium azide are added to the hemolyzed sample simply as they are or as the above-described solution, the pretreatment of the hemolyzed sample is carried out, usually by incubating the sample at 40° C. to 60° C. for 6 to 72 hours. By pretreating the sample with the tetrazolium compound and sodium azide, the measurement sensitivity can be improved as described above, and at the same time, the influence of reducing substances and the like contained in the sample on a redox reaction can be eliminated, thereby improving the accuracy of measurement. Although the tetrazolium compound contributes to the improvement in the accuracy of measurement as described above, it is necessary that sodium azide is present with the tetrazolium compound in order to achieve the improvement in measurement sensitivity as one of the objects of the present invention. By using the tetrazolium compound and sodium azide in combination, an effect peculiar to the present invention can be obtained.

Next, the pretreated hemolyzed sample containing the tetrazolium compound and sodium azide is treated with a protease. This protease treatment is carried out so that a FAOD to be used later can act on the analyte more easily. Moreover, since the protease treatment is carried out in the presence of the tetrazolium compound as described above, glycated Hb can be degraded quickly.

As the protease, serine proteases, thiol proteases, metalloproteinases, and the like can be used, for example. Specifically, trypsin, proteinase K, chymotrypsin, papain, bromelain, subtilisin, elastase, aminopeptidase, and the like can be used. Among these, proteases that degrade the glycated hemoglobin selectively, such as bromelain, papain, trypsin derived from porcine pancreas, metalloproteinases, and protease derived from *Bacillus subtilis*, are preferable. Examples of the protease derived from *Bacillus subtilis* include a product named Protease N (e.g., Fluka Chemie AG), a product named Protease N "AMANO" (Amano Enzyme Inc.), and the like. Examples of the metalloproteinases include metalloproteinase (EC 3. 4. 24. 4) derived from the genus *Bacillus* (e.g., a product named Toyoteam, manufactured by Toyobo Co., Ltd.) and the like. Among these, metalloproteinases, bromelain, and papain are more preferable, and metalloproteinases are particularly preferable. Thus, a degradation product of glycated Hb can be prepared selectively by using a protease that degrades the glycated Hb selectively. The protease treatment usually is carried out in a buffer solution, and the conditions of the treatment are determined as appropriate depending on the type of the protease used, the concentration of the glycated Hb, etc.

As the buffer solution, CHES, CAPSO, CAPS, phosphate, Tris, EPPS, HEPES buffer solutions, and the like can be used, for example. The pH of the buffer solution is, for example, in the range from 6 to 13, preferably from 8 to 12, and more preferably from 9 to 11. Moreover, the final concentration of the buffer solution in the solution subjected to the protease treatment is, for example, in the range from 1.0 to 10 mmol/l.

Specifically, when the pretreated hemolyzed sample is treated using a metalloproteinase as the protease, the protease treatment usually is carried out under the conditions as follows: the concentration of the metalloproteinase in the reaction solution in the range from 0.1 to 40 MU/l; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12.

Furthermore, when the pretreated hemolyzed sample is treated using proteinase K as the protease, the protease treatment usually is carried out under the conditions as follows: the concentration of the protease in the reaction solution in the range from 10 to 300 KU/l; the concentration of blood cells in the reaction solution in the range from 0.05 to 15 vol %; the reaction temperature in the range from 15° C. to 37° C.; the reaction period in the range from 1 minute to 24 hours; and the pH in the range from 6 to 12. Moreover, the type of the buffer solution is not particularly limited, and for example, Tris-HCl, EPPS, PIPES buffer solutions, and the like can be used.

Next, the hemolyzed sample treated with the protease is treated with a FAOD-α (degradation FAOD) catalyzing the reaction represented by Formula (1) above, more specifically the reaction represented by Formula (7) below.

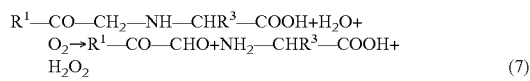

(7)

In Formula (7), $R^1$ denotes a sugar residue as in the above, and $R^3$ denotes an amino-acid side chain group as in the above.

By this treatment, the glycated amino acid having a glycated α-amino group and the glycated α-amino group of the glycated Hb degradation product contained in the hemolyzed sample are degraded.

According to this FAOD-α treatment, among various glycated amino acids, the one having a glycated side-chain amino group remains without being degraded. However, considering the ratio of the glycated amino acid having a glycated side-chain amino group to the glycated amino acids as a whole and the ratio of the same to amino acid residues having a glycated side-chain amino group in glycated Hb, it can be said that the influence of the remaining glycated amino acid is small so that the accuracy of the measurement can be improved sufficiently.

The FAOD-α treatment is carried out, for example, under the conditions as follows: the concentration of the FAOD-α in the reaction solution in the range from 10 to 5000 U/l, the concentration of the blood cells in the reaction solution in the range from 0.5 to 20 vol %, the reaction temperature in the range from 20° C. to 50° C., the reaction period in the range from 1 minute to 1 hour, and the pH in the range from 6 to 9. The FAOD-α treatment usually is carried out in a buffer solution, and the same buffer solutions as in the protease treatment also can be used in the FAOD-α treatment.

Subsequently, the hemolyzed sample treated with the FAOD-α is treated further with a FAOD-αS. As described above, the FAOD-αS acts on both a glycated α-amino group and a glycated side-chain amino group. However, since the glycated Hb degradation product has been treated with the degradation FAOD-α in advance, it is possible to cause this measurement FAOD-αS to act only on the glycated side-chain amino group of the glycated Hb degradation product.

Similarly to the above-described protease treatment, this FAOD-αS treatment preferably is carried out in a buffer solution. The type of the buffer solution is not particularly limited, and the same buffer solutions as in the protease treatment also can be used in the FAOD-αS treatment.

The FAOD-αS treatment is carried out, for example, under the conditions as follows: the concentration of the FAOD-αS in the reaction solution in the range from 10 to 30,000 U/l, the concentration of the blood cells in the reaction solution in the range from 0.1 to 5 vol %, the reaction temperature in the range from 20° C. to 50° C., the reaction period in the range from 1 minute to 1 hour, and the pH in the range from 6 to 9.

Next, the hydrogen peroxide formed by the FAOD-αS treatment is measured by causing a further redox reaction using an oxidase and a color-developing substrate.

As the color-developing substrate, DA-64, orthophenylenediamine (OPD), a substrate in which a Trinder's reagent and 4-aminoantipyrine are combined, and the like can be used, for example. Examples of the Trinder's reagent include phenols, phenol derivatives, aniline derivatives, naphthols, naphthol derivatives, naphthylamine, and naphthylamine derivatives. Furthermore, in place of the aminoantipyrine, it is possible to use aminoantipyrine derivatives, vanillin diamine sulfonic acid, methylbenzothiazolinone hydrazone (MBTH), sulfonated methylbenzothiazolinone hydrazone (SMBTH), and the like. Among these color-developing substrates, DA-64 is particularly preferable.

As the oxidase, a POD preferably is used, for example.

The redox reaction usually is carried out in a buffer solution. The conditions of the reaction are determined as appropriate depending on the concentration of the hydrogen peroxide formed, etc. The conditions are usually as follows: the concentration of the POD in the reaction solution in the range from 10 to 100,000 IU/l; the concentration of the color-developing substrate in the reaction solution in the range from 0.005 to 30 mmol/l; the reaction temperature in the range from 15° C. to 37° C.; the reaction period in the range from 0.1 to 30 minutes; and the pH in the range from 5 to 9. Moreover, the type of the buffer solution is not particularly limited, and for example, the same buffer solutions as in the protease treatment and the FAOD treatments can be used.

In the redox reaction, for example, when the color-developing substrate is used, the amount of the hydrogen peroxide can be determined by measuring the degree of the color developed (i.e. absorbance) in the reaction solution with a spectrophotometer. Then, the amount of the glycated Hb in the sample can be determined using the amount of the hydrogen peroxide thus measured and a previously prepared calibration curve showing the correlation between an amount of hydrogen peroxide and an amount of glycated Hb, for example.

The hydrogen peroxide formed by the degradation FAOD-α added first reacts with catalase present originally in the blood sample (hemolyzed sample) and is removed. Thus, it does not have any influence on the measurement of the hydrogen peroxide derived from the analyte formed by the FAOD-αS. The hydrogen peroxide formed by the FAOD-α may be removed by adding catalase. When the hydrogen peroxide is removed by the reaction with catalase, in order to prevent the hydrogen peroxide formed by the FAOD-αS treatment to be performed later from also being removed, it is preferable to add excess amounts of POD and color-developing substrate when adding the FAOD-αS. In this case, the POD preferably is added so that its activity (U) becomes 5 to 100 times that of the catalase added, for example.

During the degradation FAOD treatment of the hemolyzed sample, uricase, bilirubin oxidase, and the like, for example, further may be added to treat the hemolyzed sample in the same manner. By treating the sample with the uricase, it is possible to degrade uric acid contained in the sample. On the other hand, by treating the sample with the bilirubin oxidase, it is possible to degrade bilirubin contained in the sample. The uric acid and bilirubin have reducing power. Thus, by treating the sample in the above-described manner, the influence of reducing substances further can be eliminated, which allows the accuracy of measurement to be improved.

The amount of the uricase or bilirubin oxidase added to the sample is, for example, as follows: when the concentration of blood cells in the reaction solution is in the range from 0.2 to 2 vol %, the uricase is added so that its concentration in the reaction solution falls in the range from 0.1 to 5000 U/l, preferably from 1 to 2000 U/l, and more preferably from 5 to 1000 U/l, and the bilirubin oxidase is added so that its concentration in the reaction solution falls in the range from 0.1 to 5000 U/l, preferably from 0.5 to 1000 U/l, and more preferably from 2 to 1000 U/l. The conditions of the uricase or bilirubin oxidase treatment may be the same as those of the degradation FAOD treatment, for example.

In this measurement, the protease treatment is not necessarily performed before the degradation FAOD-α treatment as described above, and may be performed after the FAOD-α treatment, for example. As described above, the protease treatment is carried out so that the FAODs can act more easily. However, since the FAOD-α treatment is carried out in order to degrade the glycated amino acid, the effect of the present invention can be obtained sufficiently even if the glycated Hb is not degraded with the protease prior to the FAOD-α treatment.

In the method for measurement according to the present invention, the order of performing the respective treatment steps is not limited to the order described in the present embodiment, and for example, some of the treatment steps may be performed simultaneously. For example, the hemolysis treatment, the tetrazolium compound and sodium azide treatment, and the degradation FAOD treatment may be performed simultaneously, or alternatively, the protease treatment and the tetrazolium compound and sodium azide treatment may be performed simultaneously. However, the treating steps that can be performed simultaneously are not limited to these combinations.

The amount of the hydrogen peroxide can be determined not only by the above-described enzymatic method using the POD etc. but also by an electrical method, for example.

Embodiment A-2

The present embodiment is an example where the same FAOD is used to degrade a glycated amino acid and to measure glycated Hb. The FAOD used is not particularly limited, and for example, any of a FAOD-α, a FAOD-S, and a FAOD-αS may be used. In the present embodiment, measurement is carried out in the same manner as in Embodiment A-1, unless otherwise stated.

A hemolyzed sample is pretreated by adding a tetrazolium compound and sodium azide thereto, and a degradation FAOD is added to this pretreated hemolyzed sample.

Specifically, the conditions of the degradation FAOD treatment are, for example, as follows: the concentration of the degradation FAOD in the reaction solution in the range from 10 to 5000 U/l, the concentration of the blood cells in the reaction solution in the range from 0.5 to 20 vol %, the reaction temperature in the range from 20° C. to 50° C., the reaction period in the range from 1 minute to 1 hour, and the pH in the range from 6 to 9. This treatment usually is carried out in a buffer solution, and the same buffer solutions as described above also can be used in this treatment.

Next, the sample treated with the degradation FAOD is treated with a protease. A first object of this protease treatment is to degrade the glycated Hb derived from blood cells so that a measurement FAOD to be added later can act thereon more easily, as described above. A second object of the protease treatment is to inactivate the degradation FAOD by digesting it.

Since FAODs have properties that they act on glycated amino acids more easily than on glycated proteins, the glycated amino acid is degraded by the degradation FAOD treatment. However, if the glycated Hb is treated with the protease in the state where the degradation FAOD still remains, there arises a problem in that the remaining FAOD reacts with the glycation site of the glycated Hb degradation product so that the glycated Hb cannot be measured accurately. Thus, in order to prevent the remaining FAOD from reacting with the glycated Hb degradation product, the remaining FAOD is inactivated with the protease. To this end, the amount of the protease to be added needs to be sufficient to allow the degradation FAOD added first to be inactivated rapidly and also the glycated Hb to be degraded.

The type of the protease is not particularly limited, and the same proteases as described above also can be used. The conditions of the protease treatment are determined as appropriate depending on the type of the protease used, the concentration of the glycated Hb, the type and the amount of the degradation FAOD, etc.

The protease is added so that its concentration in the reaction solution of the protease treatment falls, for example, in the range from 1 to 1,000,000 KU/l, preferably from 10 to 300,000 KU/l, and more preferably from 100 to 100,000 KU/l, when the concentration of the degradation FAOD is 100 U/l.

Specifically, when the sample is treated using trypsin as the protease, the protease treatment is carried out, for example, under the conditions as follows: the concentration of the protease in the reaction solution in the range from 1000 to 30,000 KU/l; the concentration of blood cells in the reaction solution in the range from 0.2 to 5 vol %; the concentration of the FAOD in the reaction solution in the range from 10 to 1000 U/l; the reaction temperature in the range from 20° C. to 50° C.; the reaction period in the range from 10 minutes to 20 hours; and the pH in the range from 6 to 9.

Subsequently, the same FAOD as the degradation FAOD is added again as a measurement FAOD to treat the glycated Hb degradation product obtained by the protease treatment. It is necessary to add a sufficient amount of the measurement FAOD because there is a possibility that the measurement FAOD may be inactivated with the protease.

The measurement FAOD treatment also preferably is carried out in a buffer solution as in the above. The type of the buffer solution is not particularly limited, and the same buffer solutions as in the protease treatment also can be used in this measurement FAOD treatment.

The measurement FAOD is added so that its concentration in the reaction solution of this measurement FAOD treatment is, for example, in the range from 10 to 1,000,000 U/l, preferably 100 to 200,000 U/l, and more preferably 500 to 50,000 U/l, when the concentration of the protease is 10,000 KU/l.

Specifically, the conditions of the measurement FAOD treatment are, for example, as follows: the concentration of the measurement FAOD in the reaction solution in the range from 500 to 20,000 U/l; the concentration of the protease in the reaction solution in the range from 100 to 30,000 KU/l; the concentration of blood cells in the reaction solution in the range from 0.01 to 1 vol %; the reaction temperature in the range from 15° C. to 40° C.; the reaction period in the range from 1 minute to 1 hour; and the pH in the range from 6 to 9.

Embodiment A-3

The present embodiment is an example where the same FAOD is used to degrade a glycated amino acid and to measure glycated Hb. In the present embodiment, measurement is carried out in the same manner as in Embodiment A-1, unless otherwise stated.

The present embodiment differs from Embodiment A-2 in that it is not always necessary to inactivate a degradation FAOD with a protease. Because of the substrate specificity of enzymes, inactivating a FAOD with a protease can be difficult depending on the combination of the FAOD and protease. A method for measurement according to the present embodiment is effective in such a case. If a degradation FAOD added first reacts with a glycated Hb degradation product formed by the treatment with a protease, the accuracy of the measurement cannot be improved. Accordingly, it is important to adjust the ratio of a degradation FAOD to a measurement FAOD added to a sample as described later.

A hemolyzed sample is pretreated by adding a tetrazolium compound and sodium azide thereto, and a degradation FAOD is added to this pretreated hemolyzed sample.

When it is difficult to inactivate the degradation FAOD with the protease used, the degradation FAOD needs to be added in an amount such that, even if the activity of the degradation FAOD remains during the protease treatment, it does not act on the glycated Hb degradation product formed. Furthermore, in order to utilize the properties of FAODs that they act on glycated amino acids easily whereas they do not act on glycated proteins easily, the amount of the degradation FAOD to be added and the reaction period preferably are set so as to allow the degradation FAOD to act only on the glycated amino acid.

The conditions of the FAOD treatment are, for example, as follows: the concentration of the FAOD in the reaction solution in the range from 10 to 5000 U/l; the concentration of blood cells in the reaction solution in the range from 0.2 to 20 vol %; the reaction temperature in the range from 20° C. to 50° C.; the reaction period in the range from 1 minute to 1 hour; and the pH in the range from 6 to 9. This treatment usually is carried out in a buffer solution, and the same buffer solutions as described above also can be used in this treatment.

Next, the sample treated with the FAOD is treated with a protease. Since the present embodiment is an example where the protease hardly acts on the FAOD, the amount of the protease to be added is not particular limited.

The type of the protease is not particularly limited, and the same proteases as described above also can be used. The conditions of the protease treatment are determined as appropriate depending on the type of the protease used, the concentration of the glycated Hb, and the substrate specificity of the protease used with respect to the FAOD, etc., as described above.

Examples of the combination of a FAOD and a protease falling within the present embodiment include the combination of a product named FOD (Asahi Chemical Industry Co., Ltd.) and a product named Toyoteam (Toyobo Co., Ltd.) and the combination of a FAOD derived from the genus *Gibberella* and a product named Proteinase K (Hoffmann-La Roche Inc.).

When the sample is treated using trypsin as the protease, the protease treatment is carried out, for example, under the conditions as follows: the concentration of the protease in the reaction solution in the range from 100 to 6000 U/l; the concentration of blood cells in the reaction solution in the range from 0.2 to 5 vol %; the concentration of the FAOD in the reaction solution in the range from 1 to 100 U/l; the reaction temperature in the range from 20° C. to 50° C.; the reaction period in the range from 10 minutes to 20 hours; and the pH in the range from 6 to 9.

Subsequently, the same FAOD as the degradation FAOD is added again as a measurement FAOD so that it acts on the glycated Hb degradation product obtained by the protease treatment.

The measurement FAOD treatment also preferably is carried out in a buffer solution as in the above. The type of the buffer solution is not particularly limited, and the same buffer solutions as in the protease treatment also can be used in this measurement FAOD treatment.

Thus, in the present embodiment, the ratio (activity ratio A:B) of the degradation FAOD (A) to the measurement FAOD (B) added to the sample is set, for example, in the range from 1:50,000 to 1:10, preferably 1:5000 to 1:25, and more preferably 1:500 to 1:50, as described above. In the present embodiment, the degradation FAOD remains in the reaction solution unlike Embodiment A-2. However, when the ratio is in the above-described range, the remaining degradation FAOD does not act on the glycated Hb degradation product during the protease treatment to such an extent that it affects the measurement because the reaction rate of the remaining degradation FAOD is very low.

The conditions of the measurement FAOD treatment are, for example, as follows: the concentration of the measurement FAOD in the reaction solution in the range from 500 to 20,000 U/l; the concentration of the protease in the reaction solution in the range from 100 to 30,000 KU/l; the concentration of blood cells in the reaction solution in the range from 0.01 to 1 vol %; the reaction temperature in the range from 15° C. to 40° C.; the reaction period in the range from 1 minute to 1 hour; and the pH in the range from 6 to 9.

Embodiment A-4

The present embodiment is an example where hydrogen peroxide formed by the measurement FAOD treatment described above is measured using DA-64 as a color-developing substrate. In the present embodiment, measurement is carried out in the same manner as in Embodiment A-1, unless otherwise stated.

When DA-64 is used as the color-developing substrate, in order to prevent the color development error of the DA-64, final concentrations of the DA-64, the tetrazolium compound, the sodium azide, and a surfactant in the reaction solution of the redox reaction are set in the following ranges. Usually, the final concentration of the DA-64 is 1 to 10,000 µmol/l; the surfactant is 0.01 to 200 mmol/l; the tetrazolium compound is 0.05 to 20 mmol/l, and the sodium azide is 0.01 to 5 mmol/l. Preferably, the final concentration of the DA-64 is 2 to 1000 µmol/l; the surfactant is 0.05 to 30 mmol/l; the tetrazolium compound is 0.01 to 10 mmol/l; and the sodium azide is 0.02 to 2 mmol/l. More preferably, the final concentration of the DA-64 is 3 to 300 µmol/l; the surfactant is 0.1 to 10 mmol/l; the tetrazolium compound is 0.5 to 8 mmol/l; and the sodium azide is 0.08 to 0.8 mmol/l. The type of the surfactant is not particularly limited, and those described above and below may be used, for example.

The pH of this reaction solution preferably is in the range from 6.0 to 10.0, more preferably from 6.5 to 9.0, and particularly preferably from 7.0 to 8.5.

The surfactant may be added, for example, either before adding the DA-64 or simultaneously with the DA-64. When the surfactant is added to prepare a hemolyzed sample, the surfactant may be added in advance so that its concentration falls within the above-described range when the redox reaction occurs.

The DA-64 develops color by a redox reaction. Thus, by measuring the absorbance (i.e., the degree of the color developed) of the reaction solution with a spectrophotometer, for example, at a wavelength in the range from 600 to 780 nm, the amount of the hydrogen peroxide can be determined.

Embodiment A-5

Hereinafter, the method of determining a ratio of glycated Hb to total Hb according the present invention will be described in detail with reference to the following example, in which whole blood is used as a sample.

First, whole blood is hemolyzed to prepare a hemolyzed sample and the amount of glycated Hb in the sample is measured in the same manner as in Embodiment A-1. On the other hand, the amount of Hb in the sample also is measured.

The amount of Hb can be measured in the following manner, for example. First, the tetrazolium compound as described above is added to the hemolysate sample to denature the Hb. For example, when the concentration of blood cells in the hemolyzed sample is in the range from 0.2 to 2 vol %, it is preferable that the tetrazolium compound is added so that its concentration falls in the range from 0.005 to 400 mmol/l, more preferably from 0.02 to 100 mmol/l, and particularly preferably from 0.1 to 50 mmol/l. Specifically, when the tetrazolium compound is WST-3, preferably it is added so that its concentration falls in the range from 0.004 to 16 mmol/l, more preferably from 0.02 to 10 mmol/l, and particularly preferably from 0.1 to 5 mmol/l.

Although the tetrazolium compound may be used simply as it is, it preferably is used as a solution in which the tetrazolium compound is dissolved in a solvent, in terms of simplicity in operation, efficiency of the treatment, etc. The concentration of the solution can be determined as appropriate depending on the type of the tetrazolium compound (e.g. molecular weight or the like), etc. For example, the concentration is in the range of 0.01 to 120 mmol/l, preferably from 0.1 to 50 mmol/l, and more preferably from 0.2 to 20 mmol/l. As the solvent, for example, distilled water, physiological saline, buffer solutions, or the like can be used. As the buffer solutions, for example, the same buffer solutions as mentioned above can be used. Moreover, the tetrazolium compound may be used either alone or in combinations of two or more types.

The conditions of the treatment with the tetrazolium compound are not particularly limited, but may be as follows, for example: the temperature in the range from 4° C. to 50° C. and the treatment period in the range from 20 seconds to 60 minutes; preferably, the temperature in the range from 15° C. to 40° C. and the treatment period in the range from 20 seconds to 20 minutes; and more preferably, the temperature in the range from 25° C. to 37° C. and the treatment period in the range from 30 seconds to 6 minutes.

This tetrazolium compound treatment preferably is carried out in the presence of a surfactant as described above, because this can accelerate the denaturation of the Hb still further. To this end, the tetrazolium compound may be added to the sample during the hemolysis treatment for simplicity in operation and the like.

As the surfactant, polyoxyethylene ethers, polyoxyethylene phenol ethers, polyoxyethylene sorbitan alkyl esters, polyoxyethylene alkyl ethers, and the like can be used. Among these, polyoxyethylene ethers and the like are preferable. Polyoxyethylene ethers, which are represented by $[C_L H_M\text{—}O\text{—}(CH_2CH_2O)_N H]$, are compounds in which a polyoxyethylene chain and a hydrocarbon chain are linked with each other by ether linkage. Examples of the hydrocarbon chain include an alkyl group and an alkyl phenyl group. Preferably, the weight-average degree of polymerization (N) of the polyoxyethylene chain is in the range from 8 to 23 and the carbon number (L) of the hydrocarbon chain is in the range from 8 to 18; more preferably, the weight-average degree of polymerization (N) is in the range from 8 to 15 and the carbon number (L) is in the range from 8 to 16; and particularly preferably, the weight-average degree of polymerization (N) is in the range from 8 to 10 and the carbon number (L) is in the range from 8 to 14. For example, the hydrocarbon chain may be a straight chain or may have a branched chain. Specific examples of the polyoxyethylene ethers include polyoxyethylene-p-t-octylphenyl ether, polyethylene glycol (10) lauryl ether, and polyethylene glycol (9) lauryl ether.

More specifically, polyoxyethylene-p-t-octylphenyl ether such as commercially available Triton series surfactants; polyoxyethylene sorbitan alkyl ester such as commercially available Tween series surfactants; and polyoxyethylene alkyl ether such as commercially available Brij series surfactants can be used. Other than these, polyoxyethylene (10) lauryl ether; polyoxyethylene (9) lauryl ether such as a product named Nikkol BL-9 EX (the weight-average degree of polymerization (N) of polyoxyethylene is 9, manufactured by Wako Pure Chemical Industries, Ltd.); and polyoxyethylene octylphenyl ether such as a product named Tergitol NPX (the weight-average degree of polymerization (N) of polyoxyethylene is about 10.5, manufactured by Nacalai Tesque, Inc.) and a product named Tergitol NP-40 (the weight-average degree of polymerization (N) of polyoxyethylene is 20, manufactured by Nacalai Tesque, Inc.) also can be used. These surfactants also can be used as a surfactant for causing hemolysis.

The amount of the surfactant added to the hemolyzed sample is not particularly limited. However, when the concentration of blood cells in the sample is in the range from 0.2 to 1 vol %, it is preferable that the surfactant is added so that its concentration falls in the range from 0.05 to 50 mmol/l, more preferably from 0.2 to 30 mmol/l, and particularly preferably from 0.3 to 10 mmol/l. Specifically, when the surfactant is a product named Triton X-100, preferably it is added so that its concentration falls in the range from 0.2 to 100 mmol/l, more preferably from 1 to 30 mmol/l, and particularly preferably from 2 to 20 mmol/l. When the surfactant is a product named Brij 35, preferably it is added so that its concentration falls in the range from 0.1 to 50 mmol/l, more preferably from 0.5 to 20 mmol/l, and particularly preferably from 1 to 10 mmol/l.

The surfactant may be added to the sample so that, when 0.5 to 5 mmol of the tetrazolium compound is present, 0.1 to 70 mmol, preferably 0.3 to 50 mmol, and particularly preferably 0.4 to 20 mmol of the surfactant is present, for example. Specifically, when the surfactant is a product named Triton X-100, it preferably is added to the sample so that, with respect to 1 mmol of the tetrazolium compound, 0.2 to 15 mmol, more preferably 0.5 to 10 mmol, and particularly preferably from 0.7 to 5 mmol of the surfactant is present. When the surfactant is a product named Brij 35, it preferably is added to the sample so that, with respect to 1 mmol of the tetrazolium compound, 0.1 to 10 mmol, more preferably 0.2 to 8 mmol, and particularly preferably from 0.3 to 4 mmol of the surfactant is present. It is to be noted that, during the hemolysis treatment of the sample, a sufficient amount of the surfactant for accelerating the denaturation of the Hb may be added in advance.

Next, the absorbance of the denatured Hb is measured. It preferably is measured at a wavelength in the range from 520 to 670 nm, more preferably from 550 to 660 nm, as described above. When the dual-wavelength measurement is carried out using the wavelength in the above-mentioned range as the main wavelength, the sub-wavelength preferably is in the range from 730 to 900 nm, more preferably from 800 to 900 nm, and particularly preferably from 800 to 850 nm.

Using the thus-measured absorbance of the denatured Hb and a calibration curve prepared in advance, the amount of the Hb is determined. Then, using the amount of the glycated Hb measured in the above and the amount of the Hb thus determined, the ratio of the glycated Hb to the Hb can be calculated.

The calibration curve can be prepared in the following manner, for example. First, standard solutions containing different known amounts of Hb are provided. The amounts of Hb in these standard solutions are measured by the above-described method of measuring Hb and by a known method of measuring Hb. Then, based on the obtained measured values, the calibration curve is prepared. The known method is not specifically limited as long as it can measure Hb with high accuracy. However, the HiCN method as an international standard method is preferable, for example.

To carry out the absorbance measurement of the denatured Hb to determine the amount of the Hb, part of the hemolyzed sample for measuring the glycated Hb may be taken to prepare a sample for measuring the Hb. However, it is preferable to carry out the absorbance measurement as part of the processes for measuring the glycated Hb, because the measurement can be carried out quickly and simply. Specifically, in the measurement of the glycated Hb described in Embodiment A-1, for example, it is possible to measure the absorbance of the denatured Hb after the addition of the tetrazolium compound to the hemolyzed sample, after the addition of the tetrazolium compound and the sodium azide to the hemolyzed sample, after the protease treatment, after the measurement FAOD treatment, or the like.

Embodiment A-6

Hereinafter, the method of measuring HbA1c according the present invention will be described in detail with reference to the following example, in which whole blood is used as a sample.

First, a whole blood sample is provided, and the amount of glycated Hb in the sample is measured in the same manner as in Embodiment A-1. On the other hand, various glycated Hb standard solutions, in each of which an amount of HbA1c in glycated Hb is known, are provided. The amount of glycated Hb in each of these standard solutions is measured in the above-described manner. Then, a calibration curve is prepared that shows the relationship between the measured value (the amount of glycated Hb) and the amount of HbA1c in these standard solutions. As described above, there is a correlation between the measured value of the glycated Hb and the amount of HbA1c. Therefore, by substituting the measured value of the glycated Hb in the whole blood sample into this calibration curve, the amount of HbA1c in the whole blood sample can be determined.

In the preparation of the calibration curve, the measured value of the amount of glycated Hb is not limited to the value obtained finally, and may be an absorbance of the reaction solution of the POD treatment in the process for measuring the amount of glycated Hb, or an amount of hydrogen peroxide determined using this absorbance.

Next, a measuring kit according to the present invention will be described in detail with reference to the following example, in which the analyte is glycated Hb.

Embodiment B-1

The present embodiment is one example of the first measuring kit, in which a FAOD-α is used as a degradation FAOD contained in a pretreatment reagent and a FAOD-αS is used as a measurement FAOD contained in a color-developing reagent.

This measuring kit includes a pretreatment reagent containing a degradation FAOD, a protease reagent containing a protease, and a color-developing reagent containing a measurement FAOD, an oxidoreductase, and a color-developing substrate.

Each of the pretreatment reagent, the protease reagent, and the color-developing reagent can be prepared by dissolving the component(s) to be contained therein in an aqueous solvent.

(Pretreatment Reagent)

In the color-developing reaction solution obtained finally, the pretreatment reagent is diluted 10-fold to 200-fold, preferably 20-fold to 100-fold, for example. Therefore, the concentration of the FAOD and the like contained in this pretreatment reagent can be determined as appropriate depending on this diluting factor etc., for example. Furthermore, the amount of the FAOD and the like in the reaction system may be adjusted by changing the amount of the pretreatment reagent to be added to a sample depending on the amount of an analyte or a glycated amino acid to be degraded contained in the sample.

Specifically, the concentration of the degradation FAOD in the pretreatment reagent is in the range from 10 to 5000 U/l, for example.

As the aqueous solvent, although not particularly limited, water, buffer solutions containing the above-described various buffers, and the like can be used, for example. Among the above-described buffers, CHES, MOPS, TAPS, EPPS, phosphate, HEPPSO, POPSO, and borate are preferable, and CHES, MOPS, TAPS, and phosphate are more preferable. The concentration of the buffer solution is, for example, in the range from 5 to 200 mol/l, preferably 20 to 150 mol/l. Furthermore, the pH of the buffer solution is, for example, in the range from 8 to 10, preferably 8.5 to 10.

This pretreatment reagent further may contain the following components in addition to the degradation FAOD.

When the pretreatment reagent contains a surfactant, various surfactants as above described can be used, for example. However, among these surfactants, polyoxyethylene alkyl ethers and polyoxyethylene octylphenyl ethers are preferable. The concentration of the surfactant is, for example, in the range from 0.03 to 200 mmol/l, preferably 0.1 to 50 mmol/l.

When the pretreatment reagent contains uricase, its concentration is in the range from 1 to 2000 U/l, for example. On the other hand, when the pretreatment reagent contains bilirubin oxidase, its concentration is in the range from 1 to 2000 U/l, for example. The pretreatment reagent may contain both uricase and bilirubin oxidase.

(Protease Reagent)

In the color-developing solution obtained finally, the protease reagent is diluted 1.1-fold to 3-fold, for example. Therefore, as in the case of the pretreatment reagent described above, the concentration of the respective components in this protease reagent can be determined as appropriate depending on this diluting factor etc. Furthermore, the amount of the protease in the reaction system may be adjusted by changing the amount of the protease reagent to be added to a sample depending on the amount of glycated Hb in the sample etc.

As the protease, the above-described proteases can be used, for example. When the protease is a metalloproteinase, the concentration of the protease in the protease reagent is, for example, in the range from 0.5 to 100 MU/l, preferably from 1 to 40 MU/l.

As the aqueous solvent, although not particularly limited, water, buffer solutions containing the above-described various buffers, and the like can be used, for example. Among the above-described buffers, MES and MOPS are preferable, and MES is more preferable. The concentration of the buffer solution is, for example, in the range from 1 to 20 mmol/l, preferably 1 to 5 mmol/l. The pH of the buffer solution is, for example, in the range from 5.0 to 7.0, preferably 5.5 to 6.5.

This protease reagent further may contain the following components in addition to the protease.

Examples of the components other than the protease include a tetrazolium compound and sodium azide. When the protease reagent further contains a tetrazolium compound and sodium azide, the concentrations of these components are, for example, as follows: the concentration of the tetrazolium compound is in the range from 0.1 to 10 mmol/l and the concentration of the sodium azide is in the range from 0.05 to 4 mmol/l; preferably, the concentration of the tetrazolium compound is in the range from 0.6 to 5 mmol/l and the concentration of sodium azide is in the range from 0.15 to 1.8 mmol/l. Furthermore, the tetrazolium compound (C) and the sodium azide (D) preferably are added so that they are present at a ratio (molar ratio C:D) in the range from 20:3 to 20:12, more preferably from 20:5 to 20:11, and particularly preferably from 20:6 to 20:10.

When the protease is a metalloproteinase, the protease reagent further may contain a Ca compound and a Na compound. The Ca compound and the Na compound are not particularly limited as long as they ionize to $Ca^{2+}$ and $Na^+$, respectively, in the aqueous solvent. As the Ca compound, calcium chloride ($CaCl_2$), $CaSO_4$, $(CH_3COO)_2Ca$, and the like can be used, for example. Among these, $CaCl_2$ and $CaSO_4$ are preferable. On the other hand, as the Na compound, sodium chloride (NaCl), $CH_3COONa$, $Na_2SO_4$, $NaNO_3$, and the like can be used, for example. Among these, NaCl and $Na_2SO_4$ are preferable. The Ca compound and Na compound may be used either alone or in combinations of two or more types.

The concentration of the metalloproteinase is, for example, in the range from 0.5 to 100 MU/l, preferably from 1 to 40 MU/l, as described above.

The concentration of the Ca compound is in the range from 0.1 to 50 mmol/l so that the concentration of dissociated $Ca^{2+}$ becomes 0.1 to 5 mmol/l. On the other hand, the concentration of the Na compound is in the range from 5 to 1000 mmol/l, preferably from 10 to 300 mmol/l, so that the concentration of dissociated $Na^{2+}$ becomes 5 to 1000 mmol/l.

(Color-Developing Reagent)

In the color-developing solution obtained finally, the color-developing reagent is diluted 2-fold to 20-fold, preferably 3-fold to 10-fold, and more preferably 4-fold to 8-fold, for example. Therefore, as in the case of the above-described reagents, the concentration of the respective components in this color-developing reagent can be determined as appropriate depending on this diluting factor etc., for example. Furthermore, the amount of the respective components in the reaction system may be adjusted by changing the amount of the color-developing reagent to be added to a sample depending on the amount of glycated Hb in the sample or the amount of the hydrogen peroxide formed.

The concentration of the measurement FAOD in the color-developing reagent is, for example, in the range from 1 to 200 KU/l, preferably from 5 to 100 KU/l.

The concentration of the oxidoreductase in the color-developing reagent is, for example, in the range from 1 to 1000 KU/l, preferably from 10 to 200 KU/l. As the oxidoreductase, a POD can be used, as described above.

The concentration of the color-developing substrate in the color-developing reagent is, for example, in the range from 0.001 to 100 mmol/l, preferably from 0.005 to 10 mmol/l, and more preferably from 0.02 to 1 mmol/l. As the color-developing substrate, the above-described substrates can be used.

As the aqueous solvent, although not particularly limited, water, buffer solutions containing the above-described various buffers, and the like can be used, for example. Among the above-described buffers, Tris and phosphate are preferable. The concentration of the buffer solution is, for example, in the range from 20 to 1000 mmol/l, preferably 50 to 500 mmol/l. The pH of the buffer solution is, for example, in the range from 6 to 9, preferably 6.5 to 8.

(Method of Using Measuring Kit)

Hereinafter, a method of measuring glycated Hb in blood cells using such a measuring kit will be described in detail.

A hemolyzed sample is prepared from whole blood in the same manner as in Embodiment A-1, and the pretreatment reagent is added to this hemolyzed sample so that the degradation FAOD acts on a glycated amino acid in the sample to degrade it.

By the action of this degradation FAOD-α, the glycated amino acid having a glycated α-amino group and the glycated α-amino group of the glycated Hb degradation product contained in the hemolyzed sample are degraded. According to the FAOD-α treatment, among various glycated amino acids, the one having a glycated side-chain amino group remains without being degraded. However, considering the ratio of the glycated amino acid having a glycated side-chain amino group to the glycated amino acids as a whole and the ratio of the same to amino acid residues having a glycated side-chain amino group in glycated Hb, it can be said that the influence of the remaining glycated amino acid is small so that the accuracy of the measurement can be improved sufficiently.

The amount of the pretreatment reagent to be added is, for example, as follows: to 30 µl of a hemolyzed sample containing 30 to 60 vol % of blood cells, 300 to 3000 µl, preferably 600 to 2400 µl of the pretreatment reagent is added. In the pretreatment reaction solution obtained by adding the pretreatment reagent, it is preferable that 10 to 5000 Umol/l of the degradation FAOD is present, with respect to 1 vol % of blood cells. Furthermore, the pH of this reaction solution preferably is in the range from 8 to 10, more preferably from 8.5 to 10.

In this pretreatment, it is preferable that the sample is incubated after the pretreatment reagent is added thereto. The sample may be incubated, for example, at 10° C. to 37° C. for 0.1 to 20 minutes, preferably at 15° C. to 37° C. for 0.1 to 5 minutes.

When the pretreatment reagent contains a surfactant, it is not necessary to prepare a hemolyzed sample by performing the above-described hemolysis treatment separately, for example. That is, by adding the pretreatment reagent to a whole blood sample or a blood cell sample, both the hemolysis treatment by the surfactant and the degradation treatment of the glycated amino acid by the degradation FAOD can be performed simultaneously.

In this case, in the pretreatment reaction solution obtained by adding the pretreatment reagent, it is preferable that 0.05 to 50 mmol/l, more preferably 0.2 to 30 mmol/l, and particularly preferably 0.3 to 10 mmol/l of the surfactant is present, with respect to 1 vol % of blood cells.

When the pretreatment reagent contains uricase or bilirubin oxidase as described above, the pretreatment reagent preferably contains the uricase or the bilirubin oxidase so that, in the pretreatment reaction solution, 0.4 to 4000 U/l, more preferably 3 to 1500 U/l, and particularly preferably 5 to 1000 U/l of the uricase or 0.4 to 4000 U/l, more preferably 1 to 700 U/l, and particularly preferably 2 to 700 U/l of the bilirubin oxidase is present, with respect to 1 vol % of blood cells.

Next, the protease reagent is added to the pretreatment reaction solution so that the degradation FAOD acts on glycated Hb in the sample to degrade it.

The amount of the protease reagent to be added is, for example, as follows: to 10 µl of the pretreatment reaction solution containing 1 vol % of blood cells, 50 to 300 µl, preferably 60 to 180 µl of the protease reagent is added. In the protease reaction solution obtained by adding the protease reagent, it is preferable that 100 to 50,000 KU/l, more preferably 300 to 30,000 KU/l of the protease is present, with respect to 0.1 vol % of blood cells. Furthermore, the pH of this protease reaction solution preferably is in the range from 6 to 9, more preferably from 7 to 8.5.

In this protease treatment, it is preferable that the sample is incubated after the protease reagent is added thereto. The sample may be incubated, for example, at 25° C. to 37° C. for 3 to 30 minutes, preferably at 25° C. to 37° C. for 3 to 10 minutes, and more preferably at 30° C. to 37° C. for 3 to 5 minutes.

When the protease reagent contains a tetrazolium compound and sodium azide as described above, their concentrations in the protease reaction solution are, for example, as follows: when the concentration of the protease is in the range from 100 to 10,000 KU/l, the concentration of the tetrazolium compound is in the range from 0.1 to 10 mmol/l and the concentration of the sodium azide is in the range from 0.08 to 4.0 mmol/l; preferably, the concentration of the tetrazolium compound is in the range from 0.6 to 5 mmol/l and the concentration of the sodium azide is in the range from 0.15 to 1.8 mmol/l. Specifically, when the tetrazolium compound is WST-3, its concentration in the protease reaction solution preferably is in the range from 0.2 to 6 mmol/l, more preferably from 0.6 to 4 mmol/l, and particularly preferably 0.7 to 2.7 mmol/l. By adding the tetrazolium compound and the sodium azide as described above, the measurement sensitivity becomes about 1.2 to 3 times greater than in the case where they are not added.

When the protease reagent contains a metalloproteinase and further contains a Ca compound and a Na compound as described above, their concentrations in the protease reaction solution are as follows: when the concentration of the metalloproteinase is in the range from 100 to 10,000 KU/l, for example, the concentration of the Ca compound is in the range from 0.1 to 50 mmol/l and the concentration of the Na compound is in the range from 5 to 1000 mmol/l; preferably, the concentration of the Ca compound is in the range from 0.2 to 10 mmol/l and the concentration of the Na compound is in the range from 10 to 500 mol/l; and more preferably, the concentration of the Ca compound is in the range from 0.2 to 5 mmol/l and the concentration of the Na compound is in the range from 30 to 500 mol/l.

Next, the color-developing reagent is added to the pretreatment reaction solution so that the measurement FAOD acts on the glycated Hb in the sample, thereby causing the reaction represented by Formula (1) to form hydrogen peroxide. Then, a redox reaction is caused between the color-developing substrate and the hydrogen peroxide, thereby causing the color-developing substrate to develop color by oxidation.

The measurement FAOD-αS acts on both a glycated α-amino group and a glycated side-chain amino group, as described above. However, since the glycated α-amino group is degraded in advance with the degradation FAOD-α contained in the pretreatment reagent, it is possible to cause the measurement FAOD-αS to act only on the glycated side-chain amino group.

The amount of the color-developing reagent to be added is, for example, as follows: to 100 µl of the protease reaction solution, for example, 5 to 100 µl, preferably 8 to 50 µl, and more preferably 10 to 30 µl of the color-developing reagent is added. In the color-developing reaction solution obtained by adding the color-developing reagent, it is preferable that the concentration of the measurement FAOD is in the range from 0.5 to 200 KU/l, the concentration of the oxidoreductase is in the range from 1 to 1000 KU/l, and the concentration of the color-developing substrate is in the range from 0.001 to 100 mmol/l. It is more preferable that the concentration of the measurement FAOD is in the range from 1 to 100 KU/l, the concentration of the oxidoreductase is in the range from 5 to 200 KU/l, and the concentration of the color-developing substrate is in the range from 0.005 to 10 mmol/l. It is still more preferable that the concentration of the measurement FAOD is in the range from 2 to 100 KU/l, the concentration of the oxidoreductase is in the range from 5 to 200 KU/l, and the concentration of the color-developing substrate is in the range from 0.01 to 1 mmol/l. Furthermore, the pH of this color-developing reaction solution preferably is in the range from 6 to 9, more preferably from 6.5 to 8.

In this color-developing reaction, it is preferable that the sample is incubated for a predetermined period after the protease reagent is added thereto. The sample may be incubated, for example, at 15° C. to 37° C. for 1 to 30 minutes, preferably at 25° C. to 37° C. for 3 to 10 minutes, and more preferably at 30° C. to 37° C. for 3 to 5 minutes.

Next, the color developed by the color-developing substrate is measured. This can be measured, for example, by measuring the degree of the color developed (i.e. absorbance) in the color-developing reaction solution with a spectrophotometer. Then, using this absorbance, the amount of the hydrogen peroxide is determined. The amount of glycated Hb in the sample can be determined using the amount of the hydrogen peroxide thus determined and a previously prepared calibration curve showing the correlation between an amount of hydrogen peroxide and an amount of glycated Hb, for example.

The hydrogen peroxide formed by the degradation FAOD-α added first reacts with catalase present originally in the blood sample (hemolyzed sample) to be removed. Thus, it does not have any influence on the measurement of the hydrogen peroxide derived from the analyte formed by the FAOD-αS. However, in order to remove the hydrogen peroxide sufficiently, the pretreatment reagent may further contain catalase. When the hydrogen peroxide is removed by the reaction with catalase, in order to prevent the hydrogen peroxide formed by the treatment with the measurement FAOD-αS contained in the color-developing reagent to be added later from also being removed by the catalase, it is preferable that the color-developing reagent contains excess amounts of POD and color-developing substrate.

In this case, the concentration of the catalase in the pretreatment reagent is, for example, in the range from 5 to 300 U/l, preferably from 10 to 100 U/l, and more preferably from 10 to 70 U/l. Furthermore, the concentration of the catalase in the pretreatment reaction solution is, for example, in the range from 1.5 to 50 U/l, preferably from 1.5 to 30 U/l, and more preferably from 1.5 to 15 U/l. Still further, the concentration of the catalase in the color-developing reaction solution is, for example, in the range from 1 to 50 U/l, preferably from 1 to 30 U/l, and more preferably from 1 to 10 U/l.

The concentration of the POD in the color-developing reagent is, for example, in the range from 5 to 1000 KU/l, preferably from 10 to 200 KU/l, and more preferably from 20 to 200 KU/l. Furthermore, the concentration of the POD in the color-developing reaction solution is, for example, in the range from 3 to 300 KU/l, preferably from 5 to 200 KU/l, and more preferably from 10 to 100 KU/l.

The ratio (activity ratio E:F) of the catalase (E) to the POD (F) in the color-developing reaction solution is, for example, in the range from 1:2 to 1:40, preferably 1:3 to 1:20, and more preferably 1:4 to 1:10.

The concentration of the color-developing substrate in the color-developing reagent is, for example, in the range from 0.01 to 200 mol/l, preferably from 0.02 to 20 mol/l, and more preferably from 0.04 to 5 mol/l. Furthermore, the concentration of the color-developing substrate in the color-developing reaction solution is, for example, in the range from 0.001 to 100 mmol/l, preferably from 0.005 to 10 mmol/l, and more preferably from 0.01 to 1 mmol/l.

In the measurement using this measuring kit, the order of adding the respective reagents is not limited to the above-described order, and some of the reagents may be added simultaneously. Specifically, after the pretreatment reagent is added, the protease reagent and the color-developing reagent may be added to the sample simultaneously, or the color-developing reagent may be added to the sample after the pretreatment reagent and the protease reagent are added simultaneously, for example. Alternatively, after the protease reagent is added to the sample, the pretreatment reagent and then the color-developing reagent may be added, for example.

Moreover, by using a measuring kit according to the present invention, the amount of HbA1c can be measured quickly and simply, and with high accuracy as well. This is because an amount of glycated Hb measured using the measuring kit of the present invention has a strong correlation with an amount of HbA1c. Specifically, the amount of HbA1c can be determined by preparing a calibration curve based on the correlation between an amount of glycated Hb measured using the measuring kit of the present invention and an amount of HbA1c, measuring the amount of glycated Hb in a sample by the measuring kit of the present invention, and then substituting the measured value into this calibration curve.

Embodiment B-2

The present embodiment is one example of the second measuring kit, in which the same FAOD is used as a degradation FAOD contained in a pretreatment reagent and a measurement FAOD contained in a color-developing reagent. The FAOD used is not particularly limited, and for example, any of a FAOD-α, a FAOD-S, and a FAOD-αS may be used. Unless otherwise stated, the measuring kit according to the present embodiment has the same configuration as that of the measuring kit according to Embodiment B-1, and can be used in the measurement of glycated Hb in the same manner as in Embodiment B-1.

Since FAODs have properties that they act on glycated amino acids more easily than on glycated proteins, the glycated amino acid is degraded by the degradation FAOD. However, since the same FAOD is used as the degradation FAOD and the measurement FAOD unlike Embodiment B-1, there arises a problem as follows. That is, if the glycated Hb is degraded by adding the protease reagent to the pretreatment reaction solution in the state where the degradation FAOD still remains, the remaining FAOD reacts with the glycation site of the glycated Hb degradation product so that the glycated Hb cannot be measured accurately. Therefore, when using the same FAOD, it is necessary that the protease contained in the protease reagent serves not only to degrade the glycated Hb but also to inactivate the degradation FAOD remaining in the color-developing reaction solution so as to prevent the remaining degradation FAOD from reacting with the glycated Hb degradation product. To this end, the amount of the protease contained in the protease reagent needs to be sufficient to inactivate the degradation FAOD in the pretreatment reagent rapidly and to degrade the glycated Hb.

The type and the content of the protease are not particularly limited, and preferably are determined as appropriate depending on the type and the amount of the FAOD used, the substrate specificity of the protease used with respect to the FAOD, the amount and the like of the glycated Hb, the dilution ratio of the protease when the protease reagent are added to the reaction solution, etc. Examples of the combination of a FAOD and a protease include the combination of a product named FOD (Asahi Chemical Industry Co., Ltd.) and a product named Toyoteam (Toyobo Co., Ltd.) and the combination of a FAOD derived from the genus *Gibberella* and a product named Proteinase K (Hoffmann-La Roche Inc.).

Specifically, the protease reagent preferably is added so that the concentration of the protease in the protease reaction solution falls, for example, in the range from 1 to 1,000,000 KU/l, more preferably from 10 to 300,000 KU/l, and particularly preferably 100 to 100,000 KU/l, when the concentration of the degradation FAOD is 100 U/l. More specifically, when trypsin is used as the protease, the protease reagent preferably is added so that the concentration of the trypsin in the protease reaction solution falls in the range from 1000 to 30,000 KU/l, the concentration of blood cells falls in the range from 0.2 to 5 vol %, and the concentration of the degradation FAOD falls in the range from 10 to 100 U/l, for example. Furthermore, the reaction is carried out, for example, under the conditions as follows: the reaction temperature in the range from 20° C. to 50° C.; the reaction period in the range from 10 minutes to 20 hours; and the pH in the range from 6 to 9.

In the present embodiment, it is necessary to add a sufficient amount of the measurement FAOD because there is a possibility that the measurement FAOD contained in the color-developing reagent may also be inactivated with the protease.

Specifically, the color-developing reagent preferably is added so that the concentration of the measurement FAOD in the reaction solution of the measurement FAOD treatment is, for example, in the range from 10 to 1,000,000 U/l, more preferably from 100 to 200,000 U/l, and particularly preferably 500 to 50,000 U/l, when the concentration of the protease is 10,000 KU/l.

As the specific conditions of the measurement FAOD treatment, it is preferable that the color-developing reagent is added so that the concentration of the measurement FAOD in the reaction solution falls in the range from 500 to 20,000 U/l, the concentration of the protease in the reaction solution falls in the range from 100 to 30,000 KU/l, and the concentration of blood cells in the reaction solution falls in the range from 0.01 to 1 vol %. Furthermore, the reaction is carried out, for example, under the conditions as follows: the reaction temperature in the range from 15° C. to 40° C.; the reaction period in the range from 1 minute to 1 hour; and the pH in the range from 6 to 9.

Embodiment B-3

The present embodiment is one example of the third measuring kit, in which the same FAOD is used as a degradation FAOD contained in a pretreatment reagent and a measurement FAOD contained in a color-developing reagent. However, the present embodiment differs from Embodiment B-2 in that it is not always necessary to inactivate a degradation FAOD contained in the pretreatment reagent with a protease. Because of the substrate specificity of enzymes, inactivating a FAOD with a protease can be difficult depending on the combination of the FAOD and protease. A measuring kit according to the present embodiment is effective in such a case. If the degradation FAOD contained in the pretreatment reagent reacts with a glycated Hb degradation product, the accuracy of the measurement cannot be improved. Accordingly, it is important to adjust the ratio of the FAOD in the pretreatment reagent to the FAOD in the color-developing reagent, as described later.

The FAOD used in not particularly limited, and for example, any of a FAOD-α, a FAOD-S, and a FAOD-αS may be used. Unless otherwise stated, the measuring kit according to the present embodiment has the same configuration as that of the measuring kit according to Embodiment B-1, and can be used in the measurement of glycated Hb in the same manner as in Embodiment B-1.

Examples of the combination of a FAOD and a protease falling within the present embodiment include the combination of a FAOD such as a product named FOD (Asahi Chemical Industry Co., Ltd.) and a FAOD derived from the genus *Gibberella* (ARKRAY, INC., JP 8 (1996)-154672 A) and a protease such as a product named Trypsin (Sigma Chemical Co.) and a product named Proteinase K (Wako Pure Chemical Industries, Ltd.).

The degradation FAOD needs to be added in an amount such that, even if the activity of the degradation FAOD remains during the protease treatment, it does not act on the glycated Hb degradation product formed. Furthermore, in order to utilize the properties of FAODs that they act on glycated amino acids easily whereas they do not act on glycated proteins easily, the amount of the degradation FAOD to be added desirably is set so as to allow the degradation FAOD to act only on the glycated amino acid.

Specifically, the concentration of the degradation FAOD in the pretreatment reagent is, for example, in the range from 10 to 20,000 U/l, preferably from 20 to 10,000 U/l, and more preferably from 100 to 5000 U/l. On the other hand, the concentration of the measurement FAOD in the color-developing reagent is, for example, in the range from 0.5 to 200 KU/l, preferably from 1 to 100 KU/l, and more preferably from 2 to 100 KU/l.

The pretreatment reagent preferably is added so that, in the pretreatment reaction solution, the concentration of the degradation FAOD falls in the range from 10 to 5000 U/l and the concentration of the blood cells falls in the range from 0.2 to 20 vol %.

When using this measuring kit, in order to utilize the properties of FAODs that they act on glycated amino acids easily whereas they do not act on glycated proteins easily, the reaction period in the treatment with the pretreatment reagent containing the degradation FAOD preferably is set so as to allow the degradation FAOD to act only on the glycated amino acid, for example. Specifically, the treatment preferably is carried out under the conditions, for example, as follows: the reaction temperature in the range from 20° C. to 37° C. and the reaction period in the range from 1 minute to 60 minutes; more preferably the reaction temperature in the range from 25° C. to 37° C. and the reaction period in the range from 2 minutes to 30 hours, and particularly preferably the reaction temperature in the range from 30° C. to 37° C. and the reaction period in the range from 3 minutes to 10 hours.

In the present embodiment, the pretreatment reagent and color-developing reagent preferably is added so that the ratio (activity ratio G:H) of the degradation FAOD (G) to the measurement FAOD (H) in the color-developing reaction solution is, for example, in the range from 1:3 to 1:100, preferably from 1:5 to 1:50, and particularly preferably from 1:10 to 1:40. In the present embodiment, the degradation FAOD remains in the protease reaction solution unlike Embodiment B-2. However, when the ratio is in the above-described range, the remaining degradation FAOD does not act on the glycated Hb degradation product during the protease treatment to such an extent that it affects the measurement because the reaction rate of the remaining degradation FAOD is very low.

Embodiment B-4

The present embodiment is an example where DA-64 is used as a color-developing substrate contained in a color-developing reagent. Unless otherwise stated, the measuring kit according to the present embodiment has the same configuration as that of the measuring kit according to Embodiment B-1, and can be used in the measurement of glycated Hb in the same manner as in Embodiment B-1.

When the protease reagent contains a tetrazolium compound and sodium azide to improve the measurement sensitivity as described above and the color-developing reagent contains DA-64 as a color-developing substrate, the above-described color development error of the DA-64 may occur due to the presence of the tetrazolium compound and the sodium azide with the DA-64 in the color-developing reaction solution. Therefore, in order to prevent the color development error, the respective reagents preferably have the following compositions.

It is preferable that at least one of the pretreatment reagent, the protease reagent, and the color-developing reagent contains a surfactant. As the surfactant, the above-described surfactants can be used, for example.

When the pretreatment reagent contains a surfactant, the concentration of the surfactant is in the range from 0.03 to 200 mmol/l, preferably 0.1 to 50 mmol/l. When the protease reagent contains a surfactant, the concentration of the surfactant is in the range from 0.01 to 50 mmol/l, preferably 0.05 to 20 mmol/l. When the color-developing reagent contains a surfactant, the concentration of the surfactant is in the range from 0.06 to 30 mol/l, preferably 0.1 to 20 mol/l.

The respective reagents of the measuring kit may be added so that the concentrations of respective components in the color-developing reaction solution fall within the following ranges. Preferably, the concentration of the DA-64 is 0.001 to 100 mmol/l; the surfactant is 0.002 to 50 mmol/l; the tetrazolium compound is 0.1 to 10 mmol/l; and the sodium azide is 0.08 to 4 mmol/l. More preferably, the concentration of the DA-64 is 0.005 to 10 mmol/l, the surfactant is 0.005 to 20 mmol/l; the tetrazolium compound is 0.6 to 5 mmol/l; and the sodium azide is 0.15 to 1.8 mmol/l. Particularly preferably, the concentration of the DA-64 is 0.01 to 1 mmol/l; the surfactant is 0.02 to 10 mmol/l; the tetrazolium compound is 0.7 to 2.7 mmol/l; and the sodium azide is 0.2 to 1.5 mmol/l.

The pH of the color-developing reaction solution preferably is in the range from 6.0 to 9.0, more preferably from 6.5 to 8.5, and particularly preferably from 7.0 to 8.0.

The DA-64 develops color by the redox reaction. Thus, by measuring the absorbance (i.e., the degree of the color developed) of the reaction solution with a spectrophotometer, for example, at a wavelength in the range from 650 to 750 nm, the amount of the hydrogen peroxide can be determined.

EXAMPLES

Example 1

Whole blood samples were collected from patients (the number of patients: 163), and the erythrocytes in the samples were allowed to precipitate naturally and collected. Thereafter, 10 μl of the erythrocyte fractions were mixed with 600 μl of the following pretreatment reagent to prepare hemolyzed samples (n=163). Since the collected erythrocyte fractions were obtained by causing erythrocytes to precipitate naturally, the hemolyzed samples also contained components in plasma.

| (Pretreatment Reagent: pH 9.4) | |
|---|---|
| CHAPS | 50 mmol/l |
| Surfactant (product name NIKKOL-BL9EX, Nikko Chemicals Co. Ltd.) | 9 g/l |

| (Pretreatment Reagent: pH 9.4) | |
|---|---|
| FAOD (product name FAOX, Kikkoman Corporation) | 1 KU/l |

Next, 20 μl of the respective hemolyzed samples were mixed with 76 of the following protease reagent, and the resultant mixtures were incubated at 37° C. for 5 minutes. Subsequently, 19 μl of the following color-developing reagent further was added, and the resultant mixtures were incubated at 37° C. for 3 minutes. Then, the absorbance was measured at the wavelengths of 751 nm and 571 nm. For the measurement of the absorbance, an automatic analysis apparatus (product name JCA-BM 8, manufactured by Japan Electron Optics Laboratory Co. Ltd.) was used.

| (Protease Reagent: pH 5.5) | |
|---|---|
| Tetrazolium compound (product name WST-3, Dojindo Laboratories) | 2 mmol/l |
| $NaN_3$ | 0.6 mmol/l |
| NaCl | 100 mmol/l |
| $CaCl_2$ | 2 mmol/l |
| Neutral protease (ARKRAY, INC.) | 4 MU/l |
| MES | 1 mmol/l |

| (Color-Developing Reagent: pH 7.0) | |
|---|---|
| Product name DA-64 (Wako Pure Chemical Industries, Ltd.) | 80 μmol/l |
| FAOD (ARKRAY, INC.) | 36 KU/l |
| Tris-HCl | 380 mmol/l |
| $NaN_3$ | 0.5 mmol/l |

Thereafter, the thus-measured absorbances were substituted into previously prepared calibration curves showing the relationships between a Hb concentration (g/l) and absorbance and between a HbA1c concentration (g/l) and absorbance, respectively, to determine the Hb concentration and the HbA1c concentration. Then, HbA1c % was calculated using the following equation. The Hb concentration can be determined based on the absorbance measured at the wavelength of 751 nm, and the HbA1c concentration can be determined based on the absorbance measured at the wavelength of 571 nm.

HbA1c (%)=(HbA1c concentration/Hb concentration)×100

The calibration curves were prepared in the following manner. First, standard solutions with various known concentrations of Hb were provided. Then, the HbA1c concentration and the Hb concentration of these standard solutions were measured by HPLC using a HbA1c measuring apparatus (product name HA-8160, manufactured by ARKRAY, INC.). On the other hand, with respect to these standard solutions, the absorbance corresponding to the Hb concentration and the absorbance corresponding to the HbA1c concentration were measured in the same manner as described above. Based on the measured values given by the automatic analysis apparatus and the absorbances thus measured, primary regression equations were prepared, which were used as the calibration curves.

Furthermore, the value obtained by performing the measurement by HPLC method with respect to the hemolyzed samples (n=163) prepared in Example 1 was used as a control.

The results of the above-described measurements are shown in FIG. 1. FIG. 1 is a graph showing the relationship between the HbA1c (%) in Example 1 measured by the enzymatic method and the HbA1c (%) as the control obtained by HPLC. In FIG. 1, Example 1 has a correlation equation of "y=1.031x−0.09" and a correlation coefficient of "0.981".

Thus, the value obtained in Example 1 was very close to the control value. Furthermore, Example 1 exhibited the extremely high correlation coefficient (0.981) with the control. Therefore, it is understood that glycated Hb was measured with high accuracy.

INDUSTRIAL APPLICABILITY

As specifically described above, the method of measuring a glycated protein and the measuring kit according to the present invention can achieve excellent measurement accuracy because the influence of a glycated amino acid present in a sample with the glycated protein as an analyte on the measurement can be eliminated. Accordingly, by applying the present invention to, for example, the measurement of glycated Hb and HbA1c in erythrocytes, more reliable measured value can be obtained than by conventional methods, which further increases the importance of the glycated Hb and HbA1c as indicators in the diagnosis and the like of diabetes.

The invention claimed is:

1. A method of measuring the amount of a glycated protein present in a sample, comprising:
   pretreating said sample by adding an amount of a reagent containing a degradation a fructosyl amino acid oxidase (degradation FAOD) so that a glycated free amino acid that is present in the sample as a contaminant is degraded by the by the action of said degradation FAOD and the glycated protein remains in the sample;
   adding an amount of a protease reagent containing a protease to the sample to degrade said glycated protein remained in the sample and produce a degradation product of the glycated protein;
   adding an amount of a reagent comprising a measurement a fructosyl amino acid oxidase (measurement FAOD) to the sample after adding said protease reagent to cause a redox reaction between the measurement FAOD and the degradation product of the glycated protein and to generate hydrogen peroxide; and
   wherein the redox reaction is conducted in the presence of a solution containing a combination of a tetrazolium compound and sodium azide, said combination of tetrazolium compound and sodium azide being added to the sample at the same time with the protease;
   measuring the amount of hydrogen peroxide generated by the redox reaction to determine the amount of the glycated protein present in the sample,
   wherein the measurement of the amount of hydrogen peroxide comprises
      adding a color-developing substrate to allow a redox reaction between the color-developing substrate and the hydrogen peroxide generated, and
      measuring an amount of color developed by the color-developing substrate to determine the amount of the hydrogen peroxide.

2. The method according to claim 1, wherein the glycated protein is glycated hemoglobin.

3. The method according to claim 1, wherein the measurement of the amount of hydrogen peroxide further comprises
   adding N-(carboxymethylaminocarbonyl)-4,4'-bis(dimethylamino) diphenylamine sodium salt as the color-developing substrate to a reaction solution of the redox reaction in the presence of a surfactant
   wherein
      the concentration of the tetrazolium compound in the reaction solution is in a range from 0.5 to 8 mmol/l,
      the concentration of the sodium azide in the reaction solution is in a range from 0.08 to 0.8 mmol/l,
      the concentration of the surfactant in the reaction solution is in a range from 0.3 to 10 mmol/l, and
      the pH of the reaction solution is in a range from 7.0 to 8.5.

4. The method according to claim 1, wherein the degradation fructosyl amino acid oxidase which acts on said glycated free amino acid is specific for a glycated α-amino group, and the measurement fructosyl amino acid oxidase which acts on the glycated protein is specific for a glycated α-amino group and a glycated side chain of an amino acid residue.

5. The method according to claim 1, wherein said solution containing said mixture of the tetrazolium compound and the sodium azide is aged by leaving the solution to stand at a temperature in the range of from 20° C. to 60° C. for 6 to 120 hours and is then added to the sample at least before the adding of the measurement FAOD.

6. The method according to claim 1, wherein the tetrazolium compound is 2-(4-iodophenyl)-3-(2,4-dinitrophenyl)-5-(2,4-disulfophenyl)-2H-tetrazolium salt.

7. A measuring the amount of a glycated protein present in a sample kit for measuring a glycated protein, comprising:
   a pretreatment reagent for pretreating said sample, containing a degradation fructosyl amino acid oxidase;
   a protease for degrading said glycated protein reagent containing a protease wherein said protease reagent further contains a combination of a tetrazolium compound and sodium azide; and
   a color-developing reagent containing a measurement fructosyl amino acid oxidase, an oxidoreductase, and a color-developing substrate for adding to said sample after said protease reagent,
   wherein the degradation fructosyl amino acid oxidase is present in an amount suitable for degrading a glycated free amino acid present in the sample as a contaminant, and
   the measurement fructosyl amino acid oxidase is present in an amount suitable for a redox reaction with a degradation product of the glycated protein degraded by the protease.

8. The measuring kit according to claim 7, wherein the glycated protein is glycated hemoglobin.

9. The measuring kit according to claim 7, wherein the degradation fructosyl amino acid oxidase contained in the pretreatment reagent is specific for a glycated α-amino group, and the measurement fructosyl amino acid oxidase contained in the color-developing reagent is specific for a glycated α-amino group and a glycated side chain of an amino acid residue.

10. The measuring kit according to claim 7, wherein the protease is at least one protease selected from the group consisting of metalloproteinases, bromelain, papain, trypsin, proteinase K, subtilisin, and aminopeptidase.

11. The measuring kit according to claim 7, wherein the protease is at least one protease that degrades glycated hemoglobin selectively and is selected from the group consisting of metalloproteinases, bromelain, papain, trypsin derived from porcine pancreas, and protease derived from *Bacillus subtilis*.

12. The measuring kit according to claim 7, wherein, in the protease reagent, the tetrazolium compound (A) and the sodium azide (B) are present at a ratio (molar ratio A:B) in a range from 20:3 to 20:12.

13. The measuring kit according to claim 7, wherein the protease reagent contains a metalloproteinase as the protease and further contains Ca and Na, and a concentration of the metalloproteinase is in a range from 100 to 40,000 KU/l, the concentration of Ca is in a range from 0.1 to 50 mmol/l, and the concentration of Na is in a range from 5 to 1000 mmol/l.

14. The measuring kit according to claim 7, wherein the color-developing substrate is N-(carboxymethylaminocarbonyl)-4,4'-bis(dimethylamino) diphenylamine sodium salt.

15. The measuring kit according to claim 7, wherein at least one of the pretreatment reagent and the color-developing reagent further contains a surfactant.

16. The measuring kit according to claim 7, wherein the protease reagent further contains a surfactant.

17. The measuring kit according to claim 15, wherein the surfactant is at least one surfactant selected from the group consisting of polyoxyethylene ethers, polyoxyethylene phenol ethers, polyoxyethylene sorbitan alkyl esters, and polyoxyethylene alkyl ethers.

18. The measuring kit according to claim 7, wherein the pretreatment reagent further contains at least one buffer selected from the group consisting of CHES, MOPS, TAPS, EPPS, phosphate, HEPPSO, POPSO, and borate, and a pH of the pretreatment reagent is in a range from 8.0 to 10.0.

19. The measuring kit according to claim 7, wherein the color-developing reagent further contains at least one buffer selected from the group consisting of MES, Tris, phosphate, MOPS, TES, HEPES, HEPPSO, and EPPS, and a pH of the color-developing reagent in a range from 6.0 to 9.0.

20. The measuring kit according to claim 7, wherein the protease reagent further contains at least one buffer selected from the group consisting of Tris, MES, DIPSO, TES, POPSO, HEPES, MOPSO, Bis-Tris, MOPS, ADA, PIPES, ACES, and phosphate, and a pH of the protease reagent is in a range from 5.0 to 7.0.

21. The measuring kit according to claim 7, wherein the tetrazolium compound is 2-(4-iodophenyl)-3-(2,4-dinitrophenyl)-5-(2,4-disulfophenyl)-2H-tetrazolium salt.

22. The measuring kit according to claim 7, wherein the pretreatment reagent further contains at least one of uricase and bilirubin oxidase.

23. The measuring kit according to claim 7, wherein the color-developing reagent further contains sodium azide.

24. The measuring kit according to claim 18, wherein the degradation fructosyl amino acid oxidase in the pretreatment reagent is specific for a glycated α-amino group;

in the pretreatment reagent, the concentration of the first fructosyl amino acid oxidase is in a range from 10 to 5000 U/l and a concentration of the buffer is in a range from 5 to 200 mmol/l; and the pH of the pretreatment reagent is in a range from 8.0 to 10.0.

25. The measuring kit according to claim 7, wherein the protease reagent further contains Ca, Na, and a buffer;

the protease in the protease reagent is a metalloproteinase;

in the protease reagent, the concentration of the metalloproteinase is in a range from 100 to 10,000 KU/l, the concentration of the tetrazolium compound is in a range from 0.1 to 10 mmol/l, the concentration of the sodium azide is in a range from 0.08 to 4 mmol/l, a concentration of Ca is in a range from 0.1 to 50 mmol/l, the concentration of Na is in a range from 5 to 1000 mmol/l, and the concentration of the buffer is in a range from 0.1 to 500 mmol/l; and the pH of the protease reagent is in a range from 5.0 to 7.0.

26. The measuring kit according to claim 19, wherein, in the color-developing reagent, the measurement fructosyl amino acid oxidase is specific for a glycated α-amino group and a glycated side chain of an amino acid residue, the oxidoreductase is a peroxidase, and the color-developing substrate is N-(carboxymethylaminocarbonyl)-4, 4'-bis(dimethylamino) diphenylamine sodium salt;

in the color-developing reagent, the concentration of the measurement fructosyl amino acid oxidase is in a range from 100 to 50,000 U/l, the concentration of the peroxidase is in a range from 0.1 to 400 KU/l, a concentration of the N-(carboxymethylaminocarbonyl)-4,4'-bis(dimethylamino)diphenylamine sodium salt is in a range from 0.02 to 2 mmol/l, and the concentration of the buffer is in a range from 10 to 500 mol/l; and the pH of the color-developing reagent is in a range from 6 to 9.

27. The method according to claim 1, wherein the pretreatment further comprises removing hydrogen peroxide generated from a redox reaction between the degradation FAOD and the glycated free amino acid using a catalase.

* * * * *